(12) United States Patent
Hansen et al.

(10) Patent No.: US 12,064,612 B2
(45) Date of Patent: *Aug. 20, 2024

(54) SYSTEMS AND METHODS FOR INERTIAL SENSING FOR VAD DIAGNOSTICS AND CLOSED LOOP CONTROL

(71) Applicant: TC1 LLC, St. Paul, MN (US)

(72) Inventors: John Freddy Hansen, Livermore, CA (US); John Donald Hill, San Francisco, CA (US); Peter Andriola, Dublin, CA (US); Daniel I. Harjes, Carlisle, MA (US); Eric Lee, Oakland, CA (US); Gionata Valchera, Zurich (CH); Nichole Mercier, Pelham, NH (US); Urim Salltakaj, Spreitenbach (CH)

(73) Assignee: TC1 LLC, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/574,905

(22) Filed: Jan. 13, 2022

(65) Prior Publication Data
US 2022/0161016 A1    May 26, 2022

Related U.S. Application Data

(63) Continuation of application No. 16/511,641, filed on Jul. 15, 2019, now Pat. No. 11,241,570.
(Continued)

(51) Int. Cl.
*A61M 60/50*    (2021.01)
*A61M 60/148*    (2021.01)
(Continued)

(52) U.S. Cl.
CPC ........ *A61M 60/148* (2021.01); *A61M 60/165* (2021.01); *A61M 60/178* (2021.01);
(Continued)

(58) Field of Classification Search
CPC .. A61M 60/148; A61M 60/165; A61M 60/50; A61M 60/562; A61M 2205/3334;
(Continued)

(56) References Cited

U.S. PATENT DOCUMENTS 3,911,897 A    10/1975    Leachman, Jr.
5,139,517 A    8/1992    Corral
(Continued)

FOREIGN PATENT DOCUMENTS

EP    1812094    8/2007
EP    2570143    3/2013
(Continued)

OTHER PUBLICATIONS

Bedi et al., "Ventricular Arrhythmias During Left Ventricular Assist Device Support", Am J Cardiol., vol. 99, Issue 8, 2007, pp. 1151-1153.
(Continued)

*Primary Examiner* — Scott M. Getzow
(74) *Attorney, Agent, or Firm* — Kilpatrick Townsend & Stockton LLP

(57) ABSTRACT

A blood circulation assist system includes a ventricular assist device (VAD) and a controller. The VAD is attachable to a heart of a patient to pump blood from a ventricle of the heart into a blood vessel of the patient. The VAD includes an impeller, a motor stator operable to rotate the impeller, and an accelerometer generating an accelerometer output indicative of accelerations of the VAD. The controller controls operation of the motor stator to control rotational speed of the impeller based on the accelerometer output.

20 Claims, 9 Drawing Sheets

Related U.S. Application Data

(60) Provisional application No. 62/699,500, filed on Jul. 17, 2018.

(51) Int. Cl.

| | |
|---|---|
| *A61M 60/165* | (2021.01) |
| *A61M 60/178* | (2021.01) |
| *A61M 60/216* | (2021.01) |
| *A61M 60/422* | (2021.01) |
| *A61M 60/515* | (2021.01) |
| *A61M 60/538* | (2021.01) |
| *A61M 60/816* | (2021.01) |

(52) U.S. Cl.
CPC ........ *A61M 60/216* (2021.01); *A61M 60/422* (2021.01); *A61M 60/515* (2021.01); *A61M 60/538* (2021.01); *A61M 60/816* (2021.01); *A61M 2205/3334* (2013.01); *A61M 2205/50* (2013.01); *A61M 2210/125* (2013.01)

(58) Field of Classification Search
CPC ........ A61M 2205/50; A61M 2210/125; A61M 60/122; A61M 60/17; A61M 60/178; A61M 60/216–232
See application file for complete search history.

(56) References Cited

U.S. PATENT DOCUMENTS

| | | |
|---|---|---|
| 5,318,592 A | 6/1994 | Schaldach |
| 5,503,615 A | 4/1996 | Goldstein |
| 5,695,471 A | 12/1997 | Wampler |
| 5,708,346 A | 1/1998 | Schob |
| 5,888,242 A | 3/1999 | Antaki et al. |
| 6,053,705 A | 4/2000 | Schob et al. |
| 6,066,086 A | 5/2000 | Antaki et al. |
| 6,071,093 A | 6/2000 | Hart |
| 6,100,618 A | 8/2000 | Schoeb et al. |
| 6,111,520 A | 8/2000 | Allen et al. |
| 6,116,862 A | 9/2000 | Rau et al. |
| 6,186,665 B1 | 2/2001 | Maher et al. |
| 6,222,290 B1 | 4/2001 | Schob et al. |
| 6,234,772 B1 | 5/2001 | Wampler et al. |
| 6,249,067 B1 | 6/2001 | Schob et al. |
| 6,264,635 B1 | 7/2001 | Wampler et al. |
| 6,278,251 B1 | 8/2001 | Schoeb |
| 6,278,379 B1 | 8/2001 | Allen et al. |
| 6,351,048 B1 | 2/2002 | Schob et al. |
| 6,355,998 B1 | 3/2002 | Schob et al. |
| 6,585,635 B1 | 7/2003 | Aldrich |
| 6,634,224 B1 | 10/2003 | Schoeb et al. |
| 6,643,420 B2 | 11/2003 | Han et al. |
| 6,688,861 B2 | 2/2004 | Wampler |
| 6,772,011 B2 | 8/2004 | Dolgin |
| 6,855,115 B2 | 2/2005 | Fonseca et al. |
| 6,879,074 B2 | 4/2005 | Amrhein et al. |
| 6,984,201 B2 | 1/2006 | Khaghani et al. |
| 6,991,595 B2 | 1/2006 | Burke et al. |
| 7,029,433 B2 | 4/2006 | Chang |
| 7,112,903 B1 | 9/2006 | Schob |
| 7,245,117 B1 | 7/2007 | Joy et al. |
| 7,320,706 B2 | 1/2008 | Al-Najjar |
| 7,439,723 B2 | 10/2008 | Allen et al. |
| 7,498,799 B2 | 3/2009 | Allen et al. |
| 7,520,850 B2 | 4/2009 | Brockway |
| 7,550,978 B2 | 6/2009 | Joy et al. |
| 7,679,355 B2 | 3/2010 | Allen et al. |
| 7,699,586 B2 | 4/2010 | LaRose et al. |
| 7,839,153 B2 | 11/2010 | Joy et al. |
| 7,853,325 B2 | 12/2010 | Dabney et al. |
| 7,862,501 B2 | 1/2011 | Woodard |
| 7,945,333 B2 | 5/2011 | Jacobson |
| 7,963,905 B2 | 6/2011 | Salmonsen et al. |
| 7,976,271 B2 | 7/2011 | LaRose et al. |
| 7,988,728 B2 | 8/2011 | Ayre |
| 7,997,854 B2 | 8/2011 | LaRose et al. |
| 7,998,054 B2 | 8/2011 | Bolling |
| 8,007,254 B2 | 8/2011 | LaRose et al. |
| 8,145,324 B1 | 3/2012 | Stevenson et al. |
| 8,152,493 B2 | 4/2012 | LaRose et al. |
| 8,177,838 B2 | 5/2012 | Vodermayer et al. |
| 8,180,448 B2 | 5/2012 | Stevenson et al. |
| 8,224,462 B2 | 7/2012 | Westlund et al. |
| 8,246,530 B2 | 8/2012 | Sullivan |
| 8,295,939 B2 | 10/2012 | Jacobson |
| 8,323,174 B2 | 12/2012 | Jeevanandam et al. |
| 8,364,283 B2 | 1/2013 | Halperin et al. |
| 8,419,609 B2 | 4/2013 | Shambaugh, Jr. et al. |
| 8,449,444 B2 | 5/2013 | Poirier |
| 8,506,471 B2 | 8/2013 | Bourque |
| 8,543,205 B2 | 9/2013 | Ostroff |
| 8,562,508 B2 | 10/2013 | Dague et al. |
| 8,597,350 B2 | 12/2013 | Rudser et al. |
| 8,608,636 B2 | 12/2013 | Choi et al. |
| 8,652,024 B1 | 2/2014 | Yanai et al. |
| 8,657,733 B2 | 2/2014 | Ayre et al. |
| 8,668,473 B2 | 3/2014 | LaRose et al. |
| 8,682,431 B2 | 3/2014 | Callaway et al. |
| 8,712,544 B2 | 4/2014 | Dabney et al. |
| 8,771,165 B2 | 7/2014 | Choi et al. |
| 8,794,989 B2 | 8/2014 | Kearsley et al. |
| 8,852,072 B2 | 10/2014 | LaRose et al. |
| 8,852,099 B2 | 10/2014 | Von Arx et al. |
| 8,864,643 B2 | 10/2014 | Reichenbach et al. |
| 8,864,644 B2 | 10/2014 | Yomtov |
| 8,882,744 B2 | 11/2014 | Dormanen et al. |
| 8,894,561 B2 | 11/2014 | Callaway et al. |
| 8,897,887 B2 | 11/2014 | Halperin et al. |
| 9,039,595 B2 | 5/2015 | Ayre et al. |
| 9,068,572 B2 | 6/2015 | Ozaki et al. |
| 9,079,043 B2 | 7/2015 | Stark et al. |
| 9,090,271 B2 | 7/2015 | Bartonek |
| 9,091,271 B2 | 7/2015 | Bourque |
| 9,265,870 B2 | 2/2016 | Reichenbach et al. |
| 9,382,908 B2 | 7/2016 | Ozaki et al. |
| 9,387,284 B2 | 7/2016 | Heilman et al. |
| 9,433,714 B2 | 9/2016 | Voskoboynikov et al. |
| 9,579,432 B2 | 2/2017 | Tamez et al. |
| 9,579,435 B2 | 2/2017 | Yomtov |
| 9,592,327 B2 | 3/2017 | Wariar et al. |
| 9,833,552 B2 | 12/2017 | Yomtov |
| 9,901,666 B2 | 2/2018 | Cotter |
| 2005/0071001 A1 | 3/2005 | Jarvik |
| 2006/0030747 A1 | 2/2006 | Kantrowitz et al. |
| 2007/0088397 A1 | 4/2007 | Jacobson |
| 2008/0281146 A1 | 11/2008 | Morello |
| 2010/0121133 A1 | 5/2010 | Schumer |
| 2010/0241223 A1 | 9/2010 | Lee et al. |
| 2011/0178361 A1 | 7/2011 | Yomtov |
| 2011/0270331 A1 | 11/2011 | Peters et al. |
| 2013/0072846 A1 | 3/2013 | Heide et al. |
| 2013/0314047 A1 | 11/2013 | Eagle et al. |
| 2014/0012067 A1 | 1/2014 | Poirier |
| 2014/0046120 A1 | 2/2014 | Choi et al. |
| 2014/0058190 A1 | 2/2014 | Gohean et al. |
| 2014/0188148 A1 | 7/2014 | le Blanc et al. |
| 2015/0057488 A1 | 2/2015 | Yomtov |
| 2015/0073203 A1* | 3/2015 | Wariar ................ A61M 60/857 600/17 |
| 2015/0148587 A1 | 5/2015 | Bourque |
| 2015/0151032 A1 | 6/2015 | Voskoboynikov et al. |
| 2015/0174307 A1 | 6/2015 | Eckman et al. |
| 2015/0246166 A1 | 9/2015 | Greatrex et al. |
| 2015/0290374 A1 | 10/2015 | Bourque et al. |
| 2015/0328466 A1 | 11/2015 | Peters et al. |
| 2016/0058929 A1 | 3/2016 | Medvedev et al. |
| 2016/0058930 A1 | 3/2016 | Medvedev et al. |
| 2016/0101230 A1 | 4/2016 | Ochsner et al. |
| 2016/0193397 A9 | 7/2016 | Aber et al. |
| 2016/0228628 A1 | 8/2016 | Medvedev et al. |
| 2016/0263299 A1 | 9/2016 | Xu et al. |
| 2017/0021070 A1 | 1/2017 | Petersen |
| 2017/0049945 A1* | 2/2017 | Halvorsen ............ A61M 60/216 |

(56) References Cited

U.S. PATENT DOCUMENTS

| | | |
|---|---|---|
| 2017/0080138 A1 | 3/2017 | Yomtov |
| 2018/0021567 A1 | 1/2018 | An et al. |
| 2018/0050348 A1 | 2/2018 | Whitney |
| 2018/0078689 A1 | 3/2018 | Yomtov |
| 2018/0140760 A1 | 5/2018 | Cotter |
| 2018/0280599 A1 | 10/2018 | Harjes et al. |
| 2018/0280600 A1 | 10/2018 | Harjes et al. |
| 2018/0280601 A1 | 10/2018 | Harjes et al. |

FOREIGN PATENT DOCUMENTS

| | | |
|---|---|---|
| EP | 3213781 | 9/2017 |
| WO | 2004028593 | 4/2004 |
| WO | 2006055745 | 5/2006 |
| WO | 2007089500 | 8/2007 |
| WO | 2011123789 | 10/2011 |
| WO | 2013119752 | 8/2013 |
| WO | 2014207225 | 12/2014 |
| WO | 2015059158 | 4/2015 |
| WO | 2016001284 | 1/2016 |
| WO | 2016137743 | 9/2016 |
| WO | 2017117185 | 7/2017 |
| WO | 2017117215 | 7/2017 |
| WO | 2017139113 | 8/2017 |
| WO | 2018020161 | 2/2018 |

OTHER PUBLICATIONS

Brisco et al., "The Incidence, Risk, and Consequences of Atrial Arrhythmias In Patients With Continuous-flow Left Ventricular Assist Devices", J Card Surg, vol. 29, Issue 4, 2014, pp. 572-580.

Clark et al., "Hemodynamic Effects of An Irregular Sequence of Ventricular Cycle Lengths During Atrial Fibrillation", Journal of the American College of Cardiology, vol. 30, Issue 4, 2007, pp. 1039-1045.

Enriquez et al., "Clinical Impact of Atrial Fibrillation In Patients With The Heartmate Ii Left Ventricular Assist Device", Journal of the American College of Cardiology, vol. 64, Issue 18, 2014, pp. 1883-1890.

Hayward et al., "Effect of Alteration In Pump Speed on Pump Output and Left Ventricular Filling With Continuous-flow Left Ventricular Assist Device", ASAIO Journal. vol. 57, issue 6, 2011, pp. 495-500.

Maeda et al., "Predictive Control by Physical Activity Rate of a Total Artificial Heart During Exercise", Transactions of the American Society of Artificial Internal Organs, vol. 34, 1988, pp. 480-484.

Maury et al., "First Experience of Percutaneous Radio-Frequency Ablation for Atrial Flutter and Atrial Fibrillation In A Patient With Heartmate Ii Left Ventricular Assist Device", Journal of Interventional Cardiac Electrophysiology, vol. 29, Issue 1, 2010, pp. 63-67.

Oswald et al., "Implantable Defibrillator Therapy for Ventricular Tachyarrhythmia In Left Ventricular Assist Device Patients", Eur J Heart Fail., vol. 12, Issue 6, 2010, pp. 593-599.

Oz et al., "Malignant Ventricular Arrhythmias Are Well Tolerated In Patients Receiving Long-term Left Ventricular Assist Devices", Journal of the American College of Cardiology, vol. 24, Issue 7, 1994, pp. 1688-1691.

Raasch et al., "Epidemiology, Management, and Outcomes of Sustained Ventricular Arrhythmias After Continuous-flow Left Ventricular Assist Device Implantation", Am Heart J., vol. 164, Issue 3, 2012, pp. 373-378.

Ziv et al., "Effects of Left Ventricular Assist Device Therapy on Ventricular Arrhythmias", Journal of the American College of Cardiology, vol. 45, Issue 9, 2005, pp. 1428-1434.

* cited by examiner

Raw Acceleration (mg)

Mean Normalized Acceleration (mg)

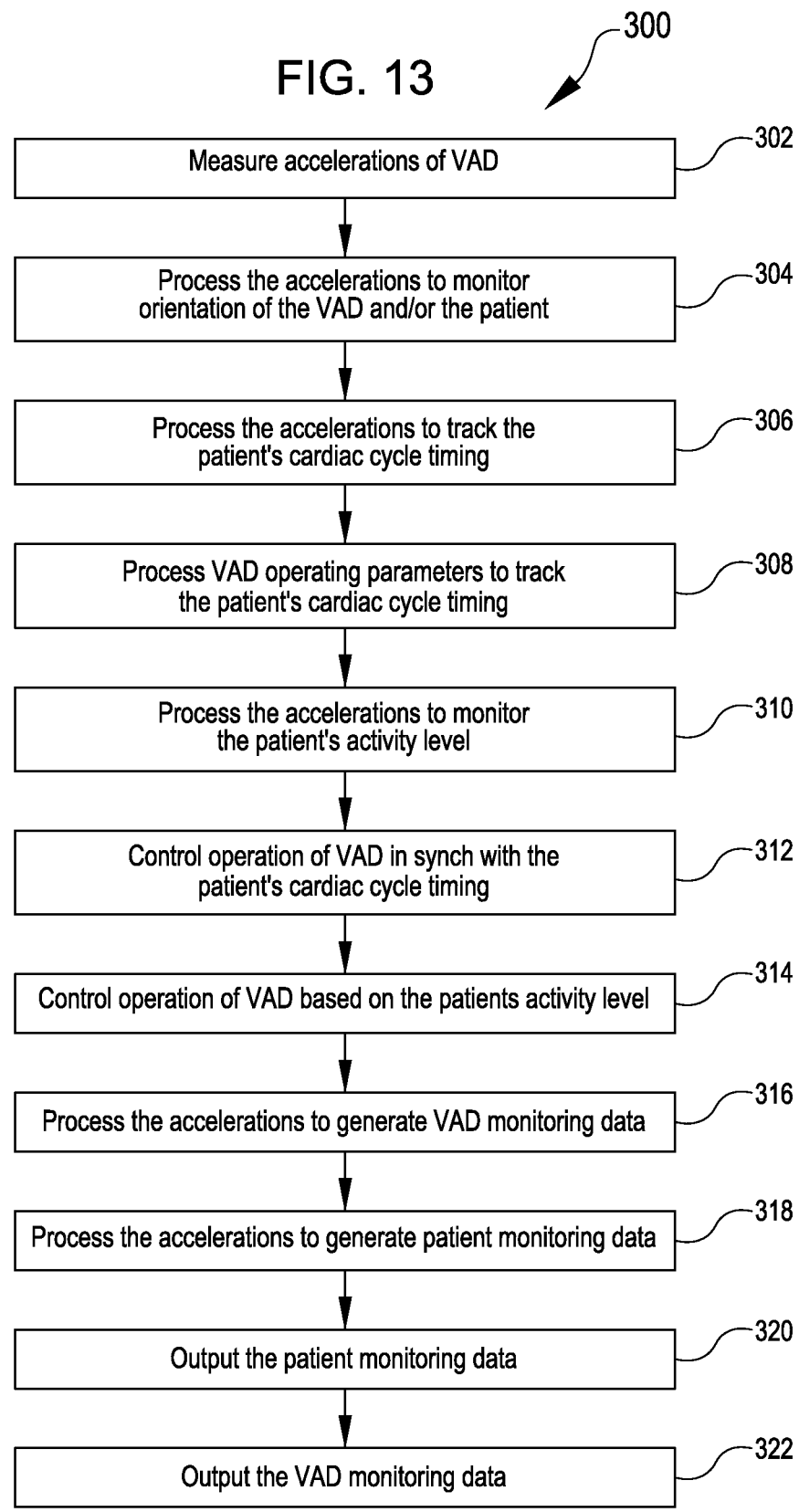

SYSTEMS AND METHODS FOR INERTIAL SENSING FOR VAD DIAGNOSTICS AND CLOSED LOOP CONTROL

CROSS REFERENCE TO RELATED APPLICATION DATA

The present application is a Continuation of U.S. patent application Ser. No. 16/511,641 filed Jul. 15, 2019 (Allowed); which claims the benefit of U.S. Provisional Appln No. 62/699,500 filed Jul. 17, 2018; the full disclosures which are incorporated herein by reference in their entirety for all purposes.

BACKGROUND

Ventricular assist devices, known as VADs, are used for both short-term (i.e., days, months) and long-term blood circulation assistance (i.e., years or a lifetime) where a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries and/or high blood pressure can leave a heart too weak to pump enough blood to the body. As symptoms worsen, advanced heart failure develops.

A patient suffering from heart failure may use a VAD while awaiting a heart transplant or as a long term destination therapy. A patient may also use a VAD while recovering from heart surgery. Thus, a VAD can supplement a weak heart (i.e., partial support) or can effectively replace the natural heart's function.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Blood circulation assist systems and related methods employ a ventricular assist device (VAD) that includes an accelerometer to measure accelerations of the VAD for use in controlling operation of the VAD, generating patient monitoring data, and/or generating VAD monitoring data. In some embodiments, the measured accelerations are processed to measure patient activity level, which is used to control the output level of the VAD based on the patient activity level. In such embodiments, the output level of the VAD can be increased in response to an increase in the patient activity level and decreased in response to a decrease in the patient activity level. In some embodiments, the measured accelerations are processed to track the patient's cardiac cycle timing, which is used to control variation in output of the VAD in synchronization with the patient's cardiac cycle timing. In some embodiments, the measured accelerations are used to generate patient monitoring data and/or VAD monitoring data. By controlling operation of the VAD based on patient activity level and/or in synch with the patient's cardiac cycle timing, the circulatory support provided is better tailored to the needs of the patient, and may thereby produce better results. Additionally, the availability of the patient monitoring data and/or the VAD tracking data may enable increased ability to diagnose patient health issues and/or VAD operational problems.

Thus, in one aspect, a blood circulation assist system includes a ventricular assist device (VAD) and a controller. The VAD is coupleable to a heart of a patient to pump blood from a ventricle of the heart into a blood vessel of the patient. The VAD includes an impeller, a motor stator operable to rotate the impeller, and an accelerometer generating an accelerometer output indicative of accelerations of the VAD. The controller controls operation of the motor stator to control rotational speed of the impeller based on the accelerometer output.

In some embodiments, the controller controls variation in output of the VAD in synch with the cardiac cycle timing of the heart. For example, in some embodiments the controller processes the accelerometer output to detect cardiac cycle timing of the heart. The cardiac cycle timing can include a heart rate of the patient and a time of occurrence for each of one or more cardiac cycle events for the heart. The controller can vary the rotational speed of the impeller in sync with the cardiac cycle timing. In some embodiments, the controller varies the rotational speed to increase a rate at which the VAD pumps blood from the ventricle to the blood vessel during ventricular systole.

In some embodiments, the controller detects the cardiac cycle timing by measuring heart wall motion. For example, the controller can process the accelerometer output to measure motion of a heart wall of the heart to which the VAD is attached. The controller can detect timing of ventricular systole of the heart based on the motion of the heart wall.

In some embodiments, the controller detects the cardiac cycle timing based on at least one heart sound. For example, the controller can process the accelerometer output to detect a time of occurrence of at least one heart sound. The controller can detect timing of ventricular systole of the heart based on the time of occurrence of the at least one heart sound. In some embodiments, the at least one heart sound includes a sound of closure of the atrioventricular valves of the heart, and/or a sound of closure of the semilunar valves of the heart.

In some embodiments, the controller detects the cardiac cycle timing by detecting variation in drive current supplied to the VAD. For example, in some embodiments the controller: (a) controls the motor stator to rotate the impeller at a constant speed throughout at least one complete cardiac cycle of the heart, (b) monitors drive current supplied to the motor stator to rotate the impeller at the constant speed, and (c) processes the monitored drive current to detect the cardiac cycle timing of the heart. In some embodiments, the controller varies the rotational speed of the impeller during ventricular systole of the heart to increase a rate at which the VAD pumps blood from the ventricle to the blood vessel.

In some embodiments, the controller synchronizes the output of the VAD with a target cardiac cycle based on detected timing of one or more previous cardiac cycles. For example, in some embodiments the controller varies the rotational speed of the impeller over a target cardiac cycle of the heart based on detected timing of one or more cardiac cycles of the heart that occur prior to the target cardiac cycle.

In some embodiments, the controller synchronizes the output of the VAD with a target cardiac cycle based on detected timing of the target cardiac cycle. For example, in some embodiments, the controller varies the rotational speed of the impeller over a target cardiac cycle of the heart based on detected timing of the target cardiac cycle.

In some embodiments, the controller controls output of the VAD based on an activity level of the patient. For example, in some embodiments, the controller: (a) processes the accelerometer output to measure an activity level of the patient, and (b) controls the rotational speed of the impeller based on the activity level. In some embodiments, the controller: (a) processes the accelerometer output to measure a respiration rate for the patient and/or a diaphragm contraction for the patient, and (b) bases the activity level on the respiration rate and/or the diaphragm contraction. In some embodiments, the controller: (a) processes the accelerometer output to measure a contraction of the ventricle, and (b) bases the activity level on the contraction of the ventricle. In some embodiments, the controller: (a) processes the accelerometer output to measure a heart rate of the patient, and (b) bases the activity level on the heart rate. In some embodiments, the controller: (a) processes the accelerometer output to detect an orientation of the patient, and (b) bases the activity level on the orientation of the patient. The activity level of the patient, on which basis the controller controls the rotational speed of the impeller, can be defined to be any suitable function of one or more of the respiration rate of the patient, the diaphragm contraction for the patient, the contraction of the ventricle, the heart rate of the patient, and the orientation of the patient.

The controller can be disposed in any suitable location. For example, in some embodiments, the controller is disposed within a housing of the VAD. In some embodiments, the blood circulation assist system further includes an external control unit operatively coupled with the VAD, and the controller is disposed within a housing of the external control unit.

Any suitable accelerometer can be employed. For example, in some embodiments, the accelerometer output is indicative of accelerations of the VAD relative to three different axes.

In another aspect, a blood circulation assist system includes a ventricular assist device (VAD) and a controller. The VAD is coupleable to a heart of a patient to pump blood from a ventricle of the heart into a blood vessel of the patient. The VAD includes an accelerometer generating an accelerometer output indicative of accelerations of the VAD. The controller processes the accelerometer output to generate patient monitoring data for the patient indicative of one or more physiological parameters of the patient.

The patient monitoring data can include any suitable data that can be generated by processing the accelerometer output. For example, in some embodiments, the patient monitoring data includes orientations of the patient and/or the VAD. In some embodiments, the patient monitoring data includes activity levels of the patient. In some embodiments, the patient monitoring data includes respiration rates and/or diaphragm contraction amplitudes. In some embodiments, the patient monitoring data includes contraction amplitudes for the ventricle. In some embodiments, the patient monitoring data includes heart rates of the patient. In some embodiments, the patient monitoring data is indicative of whether a blood clot has passed through the VAD during an acquisition time period for the patient monitoring data. In some embodiments, the patient monitoring data is indicative of whether the patient suffers from aortic insufficiency. In some embodiments, the patient monitoring data is indicative of whether arrhythmia has occurred during an acquisition time period for the patient monitoring data. In some embodiments, the patient monitoring data is indicative of whether the VAD has migrated/shifted position and/or the heart has remodeled.

In many embodiments, the blood circulation assist system includes a memory device in which the patient monitoring data is stored. In such embodiments, the patient monitoring data stored in the memory device is accessible for subsequent display and/or processing.

In another aspect, a blood circulation assist system includes a ventricular assist device (VAD) and a controller. The VAD is coupleable to a heart of a patient to pump blood from a ventricle of the heart into a blood vessel of the patient. The VAD includes an accelerometer generating an accelerometer output indicative of accelerations of the VAD. The controller processes the accelerometer output to generate VAD monitoring data indicative of one or more operational parameters of the VAD.

The VAD monitoring data can include any suitable data that can be generated by processing the accelerometer output. For example, in some embodiments: (a) the VAD includes an impeller and a motor stator operable to rotate the impeller, and (b) the VAD monitoring data is indicative of vibrations of the impeller. In some embodiments, the VAD monitoring data is indicative of whether a suction event has occurred during an acquisition time period for the VAD monitoring data.

In many embodiments, the blood circulation assist system includes a memory device in which the VAD monitoring data is stored. In such embodiments, the VAD monitoring data stored in the memory device is accessible for subsequent display and/or processing.

For a fuller understanding of the nature and advantages of the present invention, reference should be made to the ensuing detailed description and accompanying drawings.

BRIEF DESCRIPTION OF THE DRAWINGS

FIG. 13 is a simplified schematic diagram of a method of operating the VAD of FIG. 1 utilizing accelerations measured via the accelerometer of FIG. 6, in accordance with many embodiments.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Figure 1:
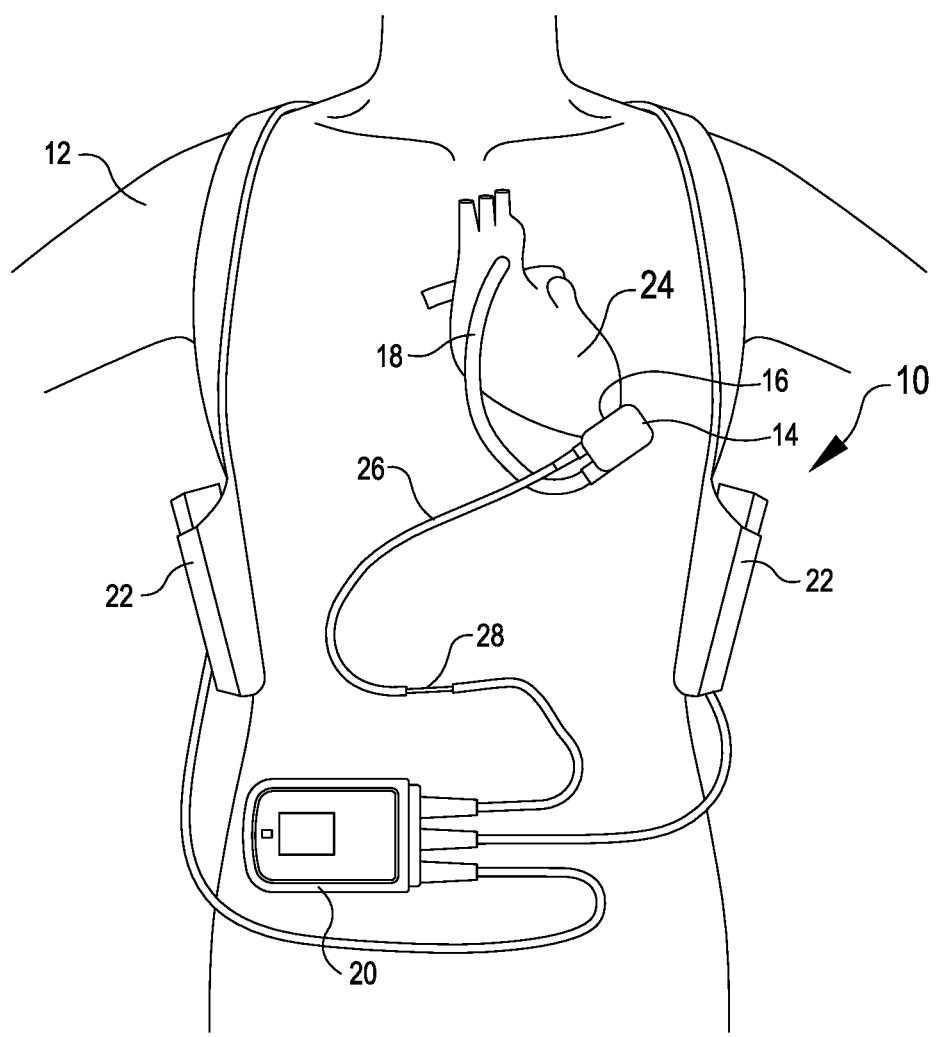
FIG. 1 is an illustration of a mechanical circulatory support system that includes a ventricular assist device (VAD) implanted in a patient's body, in accordance with many embodiments.
Figure 2:
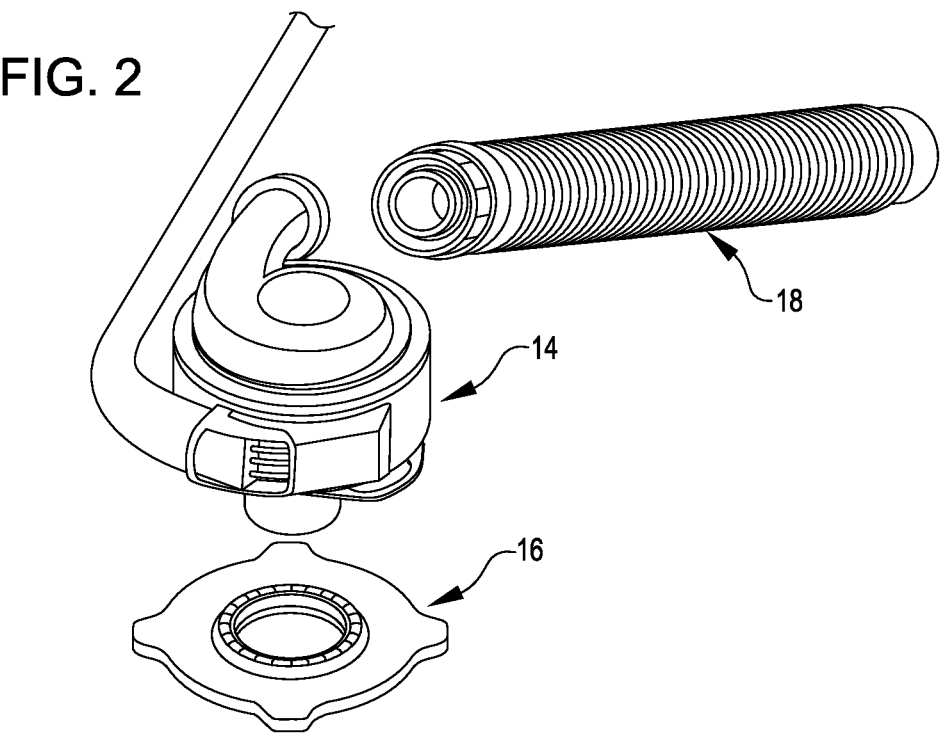
FIG. 2 is an exploded view of implanted components of the circulatory support system of FIG. 1.

Referring now to the drawings, in which like reference numerals represent like parts throughout the several views, FIG. 1 is an illustration of a mechanical circulatory support system 10 that includes a ventricular assist device (VAD) 14 implanted in a patient's body 12. The mechanical circulatory support system 10 includes the VAD 14, a ventricular cuff 16, an outflow cannula 18, an external system controller 20, and power sources 22. A VAD 14 can be attached to an apex of the left ventricle, as illustrated, or the right ventricle, or a separate VAD can be attached to each of the ventricles of the heart 24. The VAD 14 can be capable of pumping the entire flow of blood delivered to the left ventricle from the pulmonary circulation (i.e., up to 10 liters per minute). Related blood pumps applicable to the present invention are described in greater detail below and in U.S. Pat. Nos. 5,695,471, 6,071,093, 6,116,862, 6,186,665, 6,234,772, 6,264,635, 6,688,861, 7,699,586, 7,976,271, 7,997,854, 8,007,254, 8,152,493, 8,419,609, 8,652,024, 8,668,473, 8,852,072, 8,864,643, 8,882,744, 9,068,572, 9,091,271, 9,265,870, and 9,382,908, all of which are incorporated herein by reference for all purposes in their entirety. With reference to FIG. 1 and FIG. 2, the VAD 14 can be attached to the heart 24 via the ventricular cuff 16, which can be sewn to the heart 24 and coupled to the VAD 14. In the illustrated embodiment, the output of the VAD 14 connects to the ascending aorta via the outflow cannula 18 so that the VAD 14 effectively diverts blood from the left ventricle and propels it to the aorta for circulation through the rest of the patient's vascular system.

FIG. 1 illustrates the mechanical circulatory support system 10 during battery 22 powered operation. A driveline 26 that exits through the patient's abdomen 28 connects the VAD 14 to the external system controller 20, which monitors system 10 operation. Related controller systems applicable to the present invention are described in greater detail below and in U.S. Pat. Nos. 5,888,242, 6,991,595, 8,323,174, 8,449,444, 8,506,471, 8,597,350, and 8,657,733, EP 1812094, and U.S. Patent Publication Nos. 2005/0071001 and 2013/0314047, all of which are incorporated herein by reference for all purposes in their entirety. The system 10 can be powered by either one, two, or more batteries 22. It will be appreciated that although the system controller 20 and power source 22 are illustrated outside/external to the patient body 12, the driveline 26, the system controller 20 and/or the power source 22 can be partially or fully implantable within the patient 12, as separate components or integrated with the VAD 14. Examples of such modifications are further described in U.S. Pat. Nos. 8,562,508 and 9,079,043, all of which are incorporated herein by reference for all purposes in their entirety.

Figure 3:
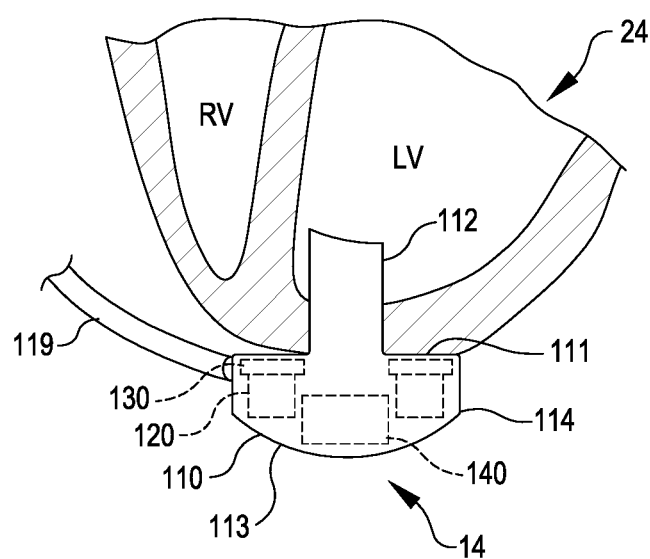
FIG. 3 is an illustration of the VAD of FIG. 1 attached to the patient's heart to augment blood pumping by the patient's left ventricle.
Figure 4:
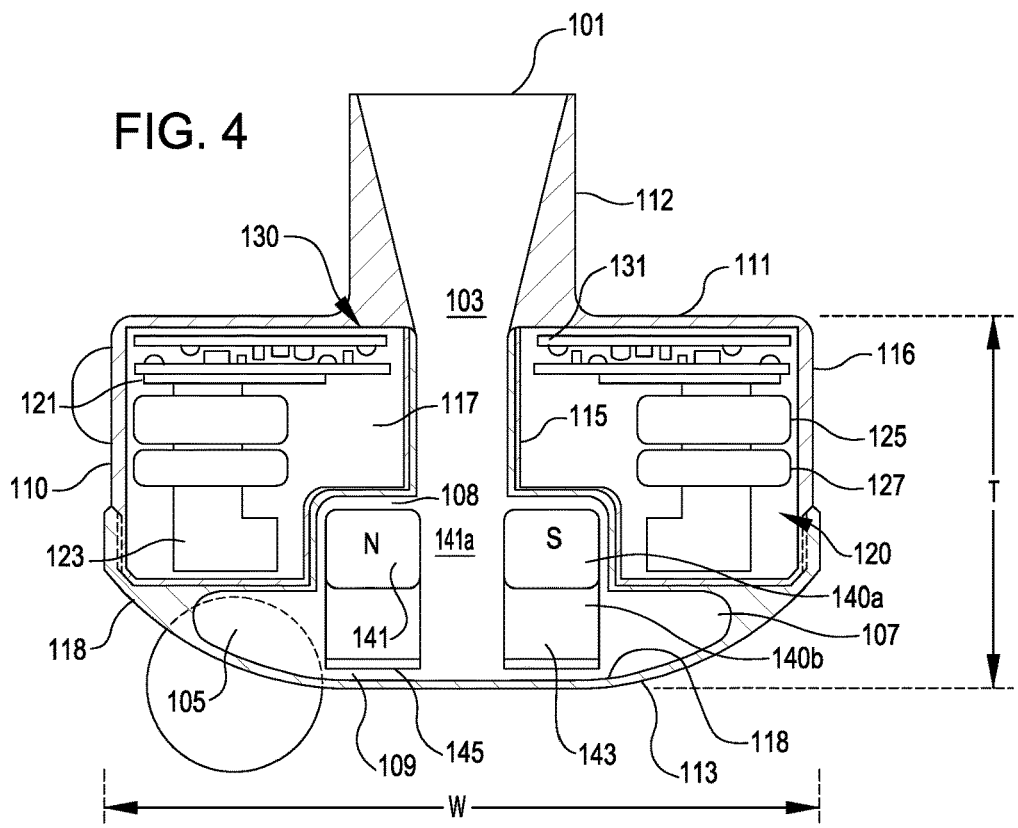
FIG. 4 is a cross-sectional view of the VAD of FIG. 3.

With reference to FIG. 3 and FIG. 4, the VAD 14 has a circular shaped housing 110 and is shown implanted within the patient 12 with a first face 111 of the housing 110 positioned against the patient's heart 24 and a second face 113 of the housing 110 facing away from the heart 24. The first face 111 of the housing 110 includes an inlet cannula 112 extending into the left ventricle LV of the heart 24. The second face 113 of the housing 110 has a chamfered edge 114 to avoid irritating other tissue that may come into contact with the VAD 14, such as the patient's diaphragm. To construct the illustrated shape of the puck-shaped housing 110 in a compact form, a stator 120 and electronics 130 of the VAD 14 are positioned on the inflow side of the housing toward first face 111, and a rotor 140 of the VAD 14 is positioned along the second face 113. This positioning of the stator 120, electronics 130, and rotor 140 permits the edge 114 to be chamfered along the contour of the rotor 140, as illustrated in at least FIG. 3 and FIG. 4, for example.

Referring to FIG. 4, the VAD 14 includes a dividing wall 115 within the housing 110 defining a blood flow conduit 103. The blood flow conduit 103 extends from an inlet opening 101 of the inlet cannula 112 through the stator 120 to an outlet opening 105 defined by the housing 110. The rotor 140 is positioned within the blood flow conduit 103. The stator 120 is disposed circumferentially about a first portion 140a of the rotor 140, for example about a permanent magnet 141. The stator 120 is also positioned relative to the rotor 140 such that, in use, blood flows within the blood flow conduit 103 through the stator 120 before reaching the rotor 140. The permanent magnet 141 has a permanent magnetic north pole N and a permanent magnetic south pole S for combined active and passive magnetic levitation of the rotor 140 and for rotation of the rotor 140. The rotor 140 also has a second portion 140b that includes impeller blades 143. The impeller blades 143 are located within a volute 107 of the blood flow conduit such that the impeller blades 143 are located proximate to the second face 113 of the housing 110.

The puck-shaped housing 110 further includes a peripheral wall 116 that extends between the first face 111 and a removable cap 118. As illustrated, the peripheral wall 116 is formed as a hollow circular cylinder having a width W between opposing portions of the peripheral wall 116. The housing 110 also has a thickness T between the first face 111 and the second face 113 that is less than the width W. The thickness T is from about 0.5 inches to about 1.5 inches, and the width W is from about 1 inch to about 4 inches. For example, the width W can be approximately 2 inches, and the thickness T can be approximately 1 inch.

The peripheral wall 116 encloses an internal compartment 117 that surrounds the dividing wall 115 and the blood flow conduit 103, with the stator 120 and the electronics 130 disposed in the internal compartment 117 about the dividing wall 115. The removable cap 118 includes the second face 113, the chamfered edge 114, and defines the outlet opening 105. The cap 118 can be threadedly engaged with the peripheral wall 116 to seal the cap 118 in engagement with the peripheral wall 116. The cap 118 includes an inner surface 118a of the cap 118 that defines the volute 107 that is in fluid communication with the outlet opening 105.

Within the internal compartment 117, the electronics 130 are positioned adjacent to the first face 111 and the stator 120 is positioned adjacent to the electronics 130 on an opposite side of the electronics 130 from the first face 111. The electronics 130 include circuit boards 131 and various components carried on the circuit boards 131 to control the operation of the VAD 14 (e.g., magnetic levitation and/or drive of the rotor) by controlling the electrical supply to the stator 120. The housing 110 is configured to receive the circuit boards 131 within the internal compartment 117 generally parallel to the first face 111 for efficient use of the space within the internal compartment 117. The circuit boards also extend radially-inward towards the dividing wall 115 and radially-outward towards the peripheral wall 116. For example, the internal compartment 117 is generally sized no larger than necessary to accommodate the circuit boards 131, and space for heat dissipation, material expansion, potting materials, and/or other elements used in installing the circuit boards 131. Thus, the external shape of the housing 110 proximate the first face 111 generally fits the shape of the circuits boards 131 closely to provide external dimensions that are not much greater than the dimensions of the circuit boards 131.

With continued reference to FIG. 4, the stator 120 includes a back iron 121 and pole pieces 123a-123f arranged at intervals around the dividing wall 115. The back iron 121 extends around the dividing wall 115 and is formed as a generally flat disc of a ferromagnetic material, such as steel, in order to conduct magnetic flux. The back iron 121 is arranged beside the control electronics 130 and provides a base for the pole pieces 123a-123f.

Each of the pole piece 123a-123f is L-shaped and has a drive coil 125 for generating an electromagnetic field to rotate the rotor 140. For example, the pole piece 123a has a first leg 124a that contacts the back iron 121 and extends from the back iron 121 towards the second face 113. The pole piece 123a can also have a second leg 124b that extends from the first leg 124a through an opening of a circuit board 131 towards the dividing wall 115 proximate the location of the permanent magnet 141 of the rotor 140. In an aspect, each of the second legs 124b of the pole pieces 123a-123f is sticking through an opening of the circuit board 131. In an aspect, each of the first legs 124a of the pole pieces 123a-123f is sticking through an opening of the circuit board 131. In an aspect, the openings of the circuit board are enclosing the first legs 124a of the pole pieces 123a-123f.

In a general aspect, the VAD 14 can include one or more Hall sensors that may provide an output voltage, which is directly proportional to a strength of a magnetic field that is located in between at least one of the pole pieces 123a-123f and the permanent magnet 141, and the output voltage may provide feedback to the control electronics 130 of the VAD 14 to determine if the rotor 140 and/or the permanent magnet 141 is not at its intended position for the operation of the VAD 14. For example, a position of the rotor 140 and/or the permanent magnet 141 can be adjusted, e.g., the rotor 140 or the permanent magnet 141 may be pushed or pulled towards a center of the blood flow conduit 103 or towards a center of the stator 120.

Each of the pole pieces 123a-123f also has a levitation coil 127 for generating an electromagnetic field to control the radial position of the rotor 140. Each of the drive coils 125 and the levitation coils 127 includes multiple windings of a conductor around the pole pieces 123a-123f. Particularly, each of the drive coils 125 is wound around two adjacent ones of the pole pieces 123, such as pole pieces 123d and 123e, and each levitation coil 127 is wound around a single pole piece. The drive coils 125 and the levitation coils 127 are wound around the first legs of the pole pieces 123, and magnetic flux generated by passing electrical current though the coils 125 and 127 during use is conducted through the first legs and the second legs of the pole pieces 123 and the back iron 121. The drive coils 125 and the levitation coils 127 of the stator 120 are arranged in opposing pairs and are controlled to drive the rotor and to radially levitate the rotor 140 by generating electromagnetic fields that interact with the permanent magnetic poles S and N of the permanent magnet 141. Because the stator 120 includes both the drive coils 125 and the levitation coils 127, only a single stator is needed to levitate the rotor 140 using only passive and active magnetic forces. The permanent magnet 141 in this configuration has only one magnetic moment and is formed from a monolithic permanent magnetic body 141. For example, the stator 120 can be controlled as discussed in U.S. Pat. No. 6,351,048, the entire contents of which are incorporated herein by reference for all purposes. The control electronics 130 and the stator 120 receive electrical power from a remote power supply via a cable 119 (FIG. 3). Further related patents, namely U.S. Pat. Nos. 5,708,346, 6,053,705, 6,100,618, 6,222,290, 6,249,067, 6,278,251, 6,351,048, 6,355,998, 6,634,224, 6,879,074, and 7,112,903, all of which are incorporated herein by reference for all purposes in their entirety.

The rotor 140 is arranged within the housing 110 such that its permanent magnet 141 is located upstream of impeller blades in a location closer to the inlet opening 101. The permanent magnet 141 is received within the blood flow conduit 103 proximate the second legs 124b of the pole pieces 123 to provide the passive axial centering force though interaction of the permanent magnet 141 and ferromagnetic material of the pole pieces 123. The permanent magnet 141 of the rotor 140 and the dividing wall 115 form a gap 108 between the permanent magnet 141 and the dividing wall 115 when the rotor 140 is centered within the dividing wall 115. The gap 108 may be from about 0.2 millimeters to about 2 millimeters. For example, the gap 108 can be approximately 1 millimeter. The north permanent magnetic pole N and the south permanent magnetic pole S of the permanent magnet 141 provide a permanent magnetic attractive force between the rotor 140 and the stator 120 that acts as a passive axial centering force that tends to maintain the rotor 140 generally centered within the stator 120 and tends to resist the rotor 140 from moving towards the first face 111 or towards the second face 113. When the gap 108 is smaller, the magnetic attractive force between the permanent magnet 141 and the stator 120 is greater, and the gap 108 is sized to allow the permanent magnet 141 to provide the passive magnetic axial centering force having a magnitude that is adequate to limit the rotor 140 from contacting the dividing wall 115 or the inner surface 118a of the cap 118. The rotor 140 also includes a shroud 145 that covers the ends of the impeller blades 143 facing the second face 113 that assists in directing blood flow into the volute 107. The shroud 145 and the inner surface 118a of the cap 118 form a gap 109 between the shroud 145 and the inner surface 118a when the rotor 140 is levitated by the stator 120. The gap 109 is from about 0.2 millimeters to about 2 millimeters. For example, the gap 109 is approximately 1 millimeter.

As blood flows through the blood flow conduit 103, blood flows through a central aperture 141a formed through the permanent magnet 141. Blood also flows through the gap 108 between the rotor 140 and the dividing wall 115 and through the gap 109 between the shroud 145 and the inner surface 108a of the cap 118. The gaps 108 and 109 are large enough to allow adequate blood flow to limit clot formation that may occur if the blood is allowed to become stagnant. The gaps 108 and 109 are also large enough to limit pressure forces on the blood cells such that the blood is not damaged when flowing through the VAD 14. As a result of the size of the gaps 108 and 109 limiting pressure forces on the blood cells, the gaps 108 and 109 are too large to provide a meaningful hydrodynamic suspension effect. That is to say, the blood does not act as a bearing within the gaps 108 and 109, and the rotor is only magnetically-levitated. In various embodiments, the gaps 108 and 109 are sized and dimensioned so the blood flowing through the gaps forms a film that provides a hydrodynamic suspension effect. In this manner, the rotor can be suspended by magnetic forces, hydrodynamic forces, or both.

Because the rotor 140 is radially suspended by active control of the levitation coils 127 as discussed above, and because the rotor 140 is axially suspended by passive interaction of the permanent magnet 141 and the stator 120, no magnetic-field generating rotor levitation components are needed proximate the second face 113. The incorporation of all the components for rotor levitation in the stator 120 (i.e., the levitation coils 127 and the pole pieces 123) allows the cap 118 to be contoured to the shape of the impeller blades 143 and the volute 107. Additionally, incorporation of all the rotor levitation components in the stator 120 eliminates the need for electrical connectors extending from the compartment 117 to the cap 118, which allows the cap to be easily installed and/or removed and eliminates potential sources of pump failure.

In use, the drive coils 125 of the stator 120 generates electromagnetic fields through the pole pieces 123 that selectively attract and repel the magnetic north pole N and the magnetic south pole S of the rotor 140 to cause the rotor 140 to rotate within stator 120. For example, the one or more Hall sensors may sense a current position of the rotor 140 and/or the permanent magnet 141, wherein the output voltage of the one or more Hall sensors may be used to selectively attract and repel the magnetic north pole N and the magnetic south pole S of the rotor 140 to cause the rotor 140 to rotate within stator 120. As the rotor 140 rotates, the impeller blades 143 force blood into the volute 107 such that blood is forced out of the outlet opening 105. Additionally, the rotor draws blood into VAD 14 through the inlet opening 101. As blood is drawn into the blood pump by rotation of the impeller blades 143 of the rotor 140, the blood flows through the inlet opening 101 and flows through the control electronics 130 and the stator 120 toward the rotor 140. Blood flows through the aperture 141a of the permanent magnet 141 and between the impeller blades 143, the shroud 145, and the permanent magnet 141, and into the volute 107. Blood also flows around the rotor 140, through the gap 108 and through the gap 109 between the shroud 145 and the inner surface 118a of the cap 118. The blood exits the volute 107 through the outlet opening 105, which may be coupled to an outflow cannula.

Figure 5:
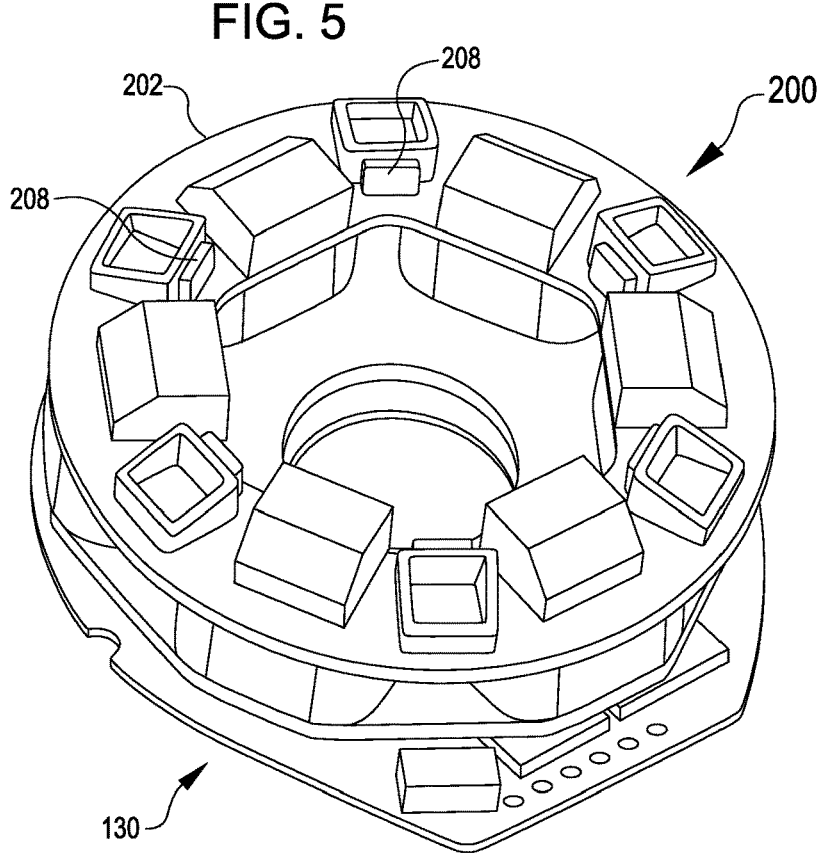
FIG. 5 is an illustration of an embodiment of a control unit for the VAD of FIG. 3.

FIG. 5 shows a Hall Sensor assembly 200 for the VAD 14, in accordance with many embodiments. The Hall Sensor assembly 200 includes a printed circuit board (PCB) 202 and six individual Hall Effect sensors 208 supported by the printed circuit board 202. The Hall Effect sensors 208 are configured to transduce a position of the rotor 140 of the VAD 14. In the illustrated embodiment, the Hall Effect sensors 208 are supported so as to be standing orthogonally relative to the PCB 202 and a longest edge of each of the Hall Effect sensors 208 is aligned to possess an orthogonal component with respect to the surface of the PCB 202. Each of the Hall Effect sensors 208 generates an output voltage, which is directly proportional to a strength of a magnetic field that is located in between at least one of the pole pieces 123a-123f and the permanent magnet 141. The voltage output by each of the Hall Effect sensors 208 is received by the control electronics 130, which processes the sensor output voltages to determine the position and orientation of the rotor 140. The determined position and orientation of the rotor 140 is used to determine if the rotor 140 is not at its intended position for the operation of the VAD 14. For example, a position of the rotor 140 and/or the permanent magnet 141 may be adjusted, for example, the rotor 140 or the permanent magnet 141 may be pushed or pulled towards a center of the blood flow conduit 103 or towards a center of the stator 120. The determined position of the rotor 140 can also be used to determine rotor eccentricity or a target rotor eccentricity, which can be used as described in U.S. Pat. No. 9,901,666, all of which is incorporated herein by reference for all purposes in its entirety, to estimate flow rate of blood pumped by the VAD 14.

Figure 6:
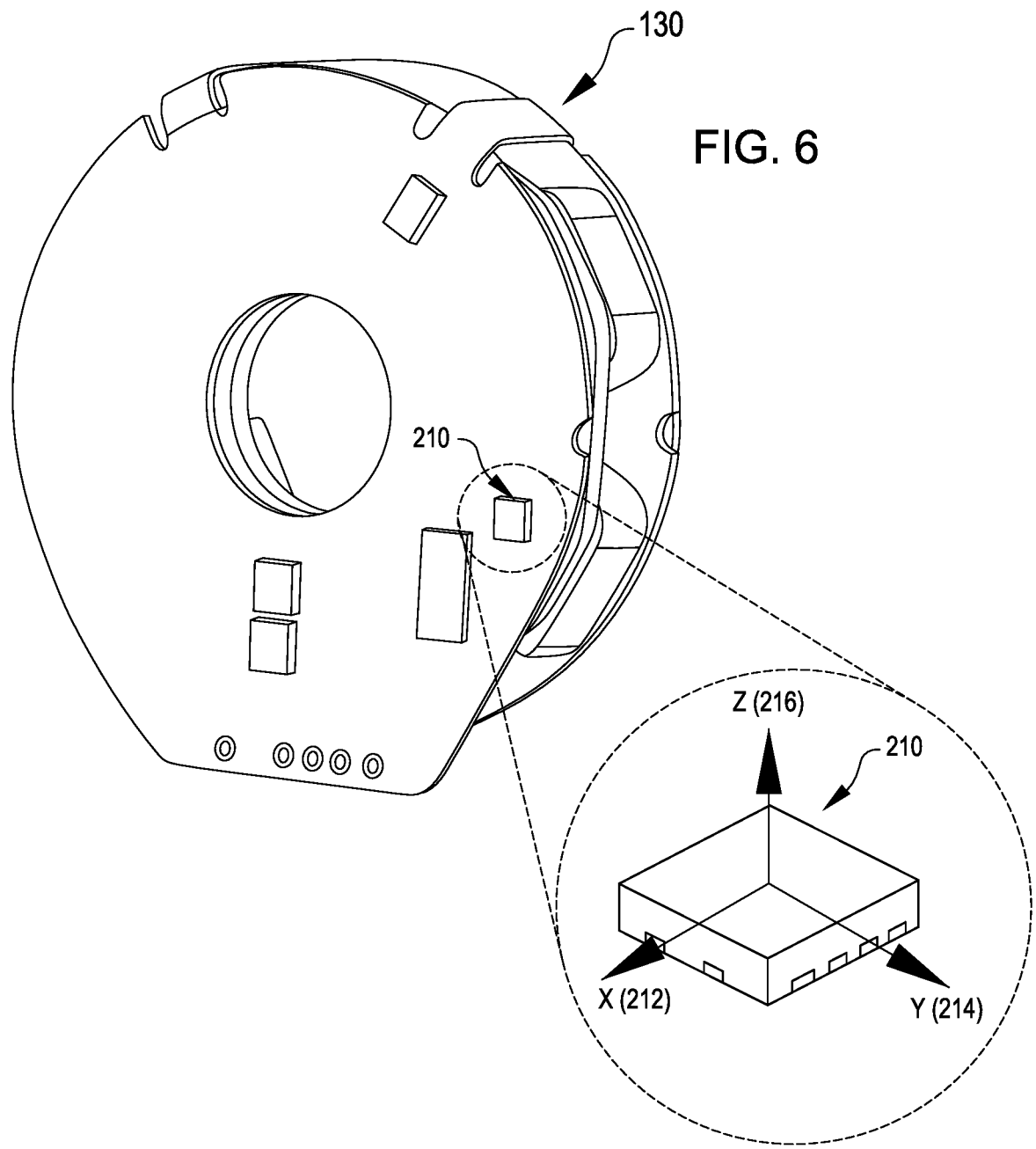
FIG. 6 is a heart-side view of the control unit of FIG. 5 showing a three-axis accelerometer included in the control unit, in accordance with many embodiments.

FIG. 6 is a heart-side view of the control electronics 130 showing an accelerometer 210 included in the control electronics 130, in accordance with many embodiments. In the many embodiments, the accelerometer 210 is a three-axis accelerometer that measures accelerations experienced by the control electronics 130 (and thereby the VAD 14) in three orthogonal axes (i.e., an X-axis 212, a Y-axis 214, and a Z-axis 216). In the illustrated embodiment, the X-axis 212 and the Y-axis 214 are each oriented orthogonal to an axis of rotation of the rotor 140, and the Z-axis 216 is parallel to the axis of rotation of the rotor 140.

Figure 7:
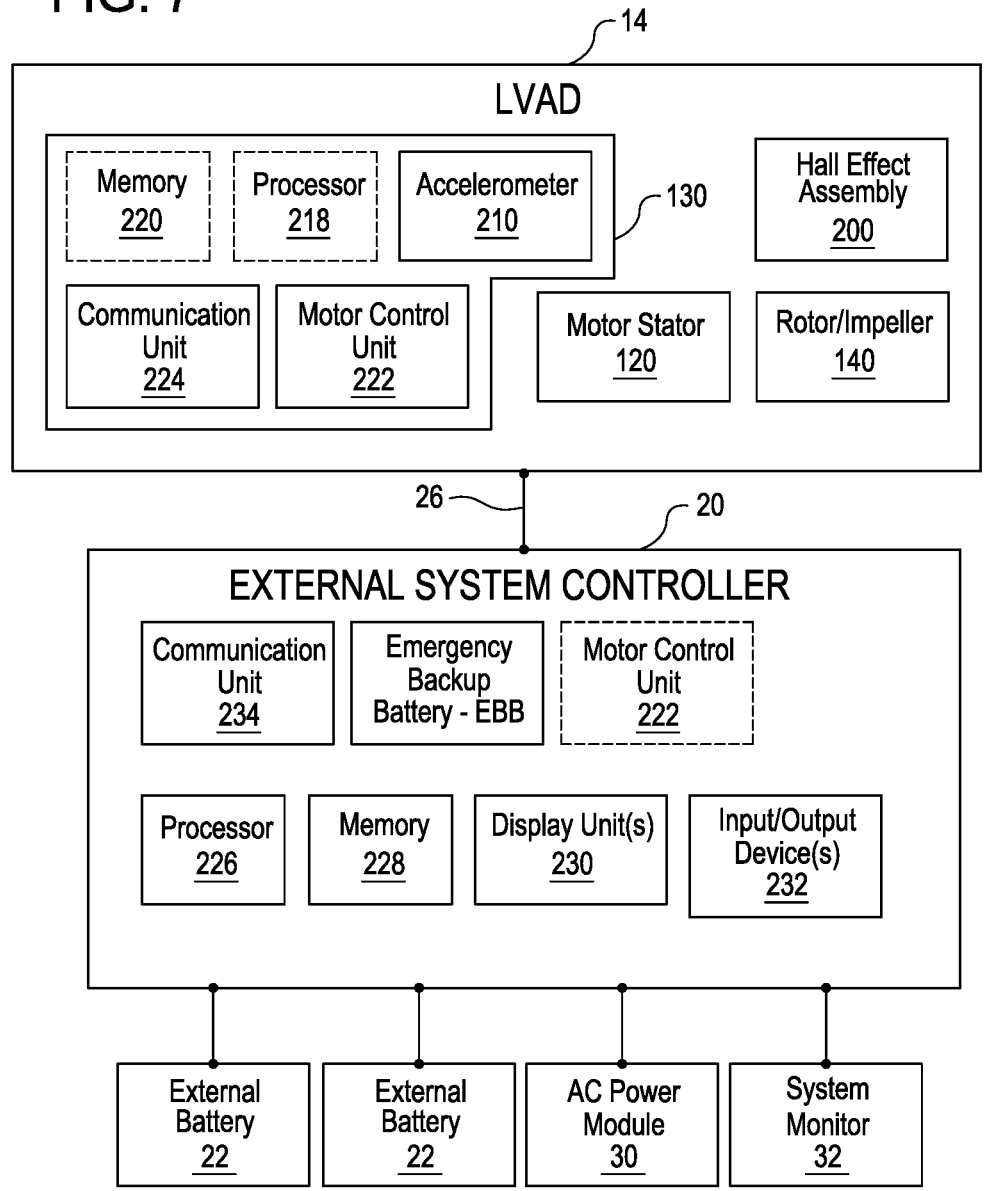
FIG. 7 is a schematic diagram of a control system architecture of the mechanical support system of FIG. 1.

FIG. 7 is a schematic diagram of a control system architecture of the mechanical support system 10. The driveline 26 couples the implanted VAD 14 to the external system controller 20, which monitors system operation via various software applications.

The VAD 14 includes the control electronics 130, the Hall Effect Sensor assembly 200, the motor stator 120, the rotor/impeller 140. In the illustrated embodiment, the control electronics include a processor 218, a memory device 220 (which can include read-only memory and/or random access-memory), the accelerometer 210, a motor control unit 222, and a communication unit 224. In some embodiments, the memory device 220 stores one or more software applications that are executable by the processor 218 for various functions. For example, the one or more software applications can effectuate control the motor control unit 222 to effectuate radial levitation and rotational drive of the rotor 140 during operation. In some embodiments, the one or more programs effectuate processing of output from the accelerometer 210 and/or operational parameters for the VAD 14 (e.g., drive current, rotational speed, flow rate, pressure differential across the impeller) as described herein to detect and/or measure patient physiological events and/or activity (e.g., patient orientation, patient activity level, heart wall motion, heart sounds, heart rate, respiratory rate, diaphragm contraction, cardiac cycle timing). The one or more programs can effectuate control of the motor control unit 222 to synchronize variation in output of the VAD 14 with the patient's cardiac cycle timing as described herein. For example, the output of the VAD 14 can be increased over a period of time during ventricular systole so as to augment pumping of blood that occurs via contraction of the ventricle, thereby reducing the associated load on the ventricle. The one or more programs can effectuate control of the motor control unit 222 to vary output of the VAD 14 based on patient activity level. For example, in many embodiments, the output of the VAD 14 is increased in response to increased patient activity and decreased in response to decreased patient activity. The one or more programs can also be used to effectuate processing of the output from the accelerometer 210 and/or the operational parameters for the VAD 14 to generate patient monitoring data and/or VAD monitoring data as described herein. The communication unit 224 provides for wired and/or wireless communication between the VAD 14 and the external system controller 20. In some embodiments, the motor control unit 222 is included in the VAD 14. In other embodiments, the motor control unit 222 is included in the external system controller 20.

The external system controller 20 can in turn be coupled to the batteries 22 or an AC power module 30 that connects to an AC electrical outlet. The external system controller 20 can include a processor 226, a memory device 228 (which can include read-only memory and/or random access-memory), an emergency backup battery (EBB) to power the system (e.g., when the batteries 22 are depleted), one or more display units 230, one or more input/output devices 232, and a communication unit 234, which can have Bluetooth capabilities for wireless data communication. An external computer having a system monitor 32 (which can be operated by a clinician or patient) may further be coupled to the circulatory support system 10 for configuring the external system controller 20, the implanted VAD 14, and/or patient specific parameters; updating software on the external system controller 20 and/or the implanted VAD 14; monitoring system operation; and/or as a conduit for system inputs or outputs.

In some embodiments, the memory device 228 stores one or more software applications that are executable by the processor 226 for various functions. For example, the one or more software applications can effectuate control the motor control unit 222 to effectuate radial levitation and rotational drive of the rotor 140 during operation. In some embodiments, the one or more programs effectuate processing of output from the accelerometer 210 and/or operational parameters for the VAD 14 (e.g., drive current, rotational speed, flow rate, pressure differential across the impeller) as described herein to detect and/or measure patient physiological events and/or activity (e.g., patient orientation, patient activity level, heart wall motion, heart sounds, heart rate, respiratory rate, diaphragm contraction, cardiac cycle timing). The one or more programs can effectuate control of the motor control unit 222 to synchronize variation in output of the VAD 14 with the patient's cardiac cycle timing as described herein. For example, the output of the VAD 14 can be increased over a period of time during ventricular systole so as to augment pumping of blood that occurs via contraction of the ventricle, thereby reducing the associated load on the ventricle. The one or more programs can effectuate control of the motor control unit 222 to vary output of the VAD 14 based on patient activity level. For example, in many embodiments, the output of the VAD 14 is increased in response to increased patient activity and decreased in response to decreased patient activity. The one or more programs can also be used to effectuate processing of the output from the accelerometer 210 and/or the operational parameters for the VAD 14 to generate patient monitoring data and/or VAD monitoring data as described herein. The communication unit 234 provides for wired and/or wireless communication between the external system controller 20 and the VAD 14 and/or the system monitor 32.

VAD Accelerations

Figure 8:
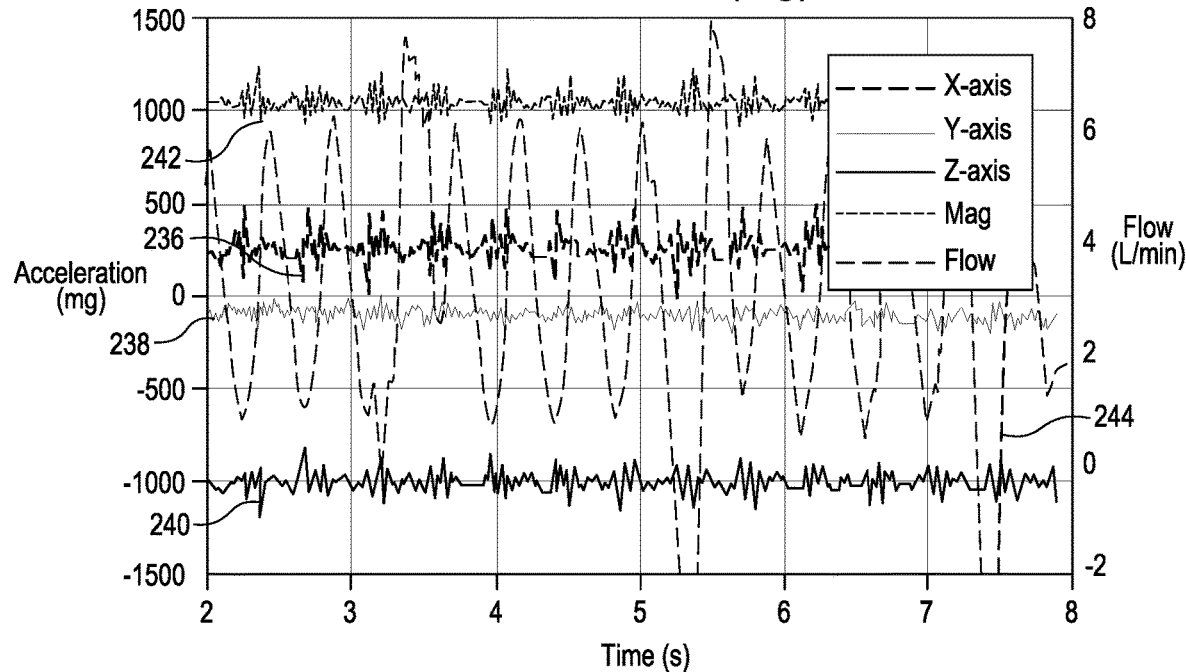
FIG. 8 is a plot of raw accelerations of the VAD generated via the three-axis accelerometer of FIG. 6.

FIG. 8 is a plot of raw accelerations of the VAD 14 measured by the three-axis accelerometer 210 during an animal study. The raw accelerations shown include X-axis acceleration 236, Y-axis acceleration 238, Z-axis acceleration 240, and a magnitude 242 of the raw acceleration. FIG. 8 also shows a flow rate 244 of the VAD 14 during the measurement of the raw accelerations.

Figure 9:
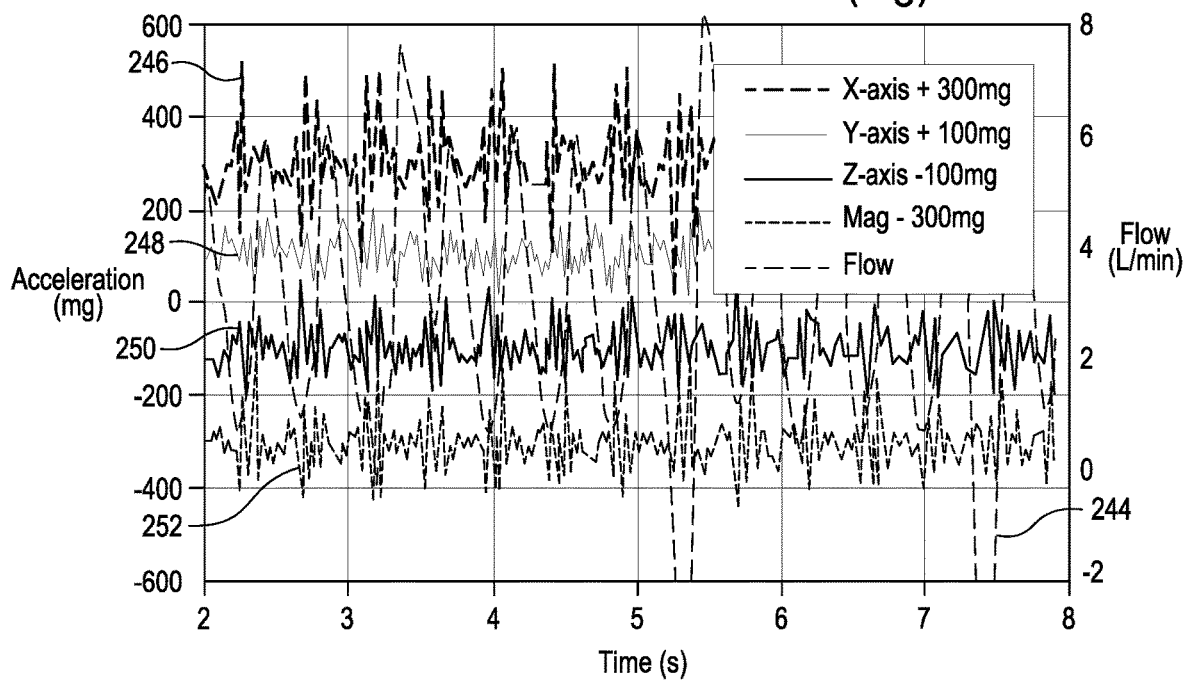
FIG. 9 is a plot of mean normalized accelerations of the VAD generated from the raw accelerations of FIG. 8.

FIG. 9 is a plot of mean normalized accelerations of the VAD 14 generated from the raw accelerations of FIG. 8. The mean normalized accelerations shown include X-axis mean normalized acceleration 246, Y-axis mean normalized acceleration 248, Z-axis mean normalized acceleration 250, and a magnitude 252 of the mean normalized acceleration. Each of the mean accelerations was produced by subtracting the corresponding average acceleration over the entire sample period from the corresponding raw acceleration plot (so that the resulting average is zero). FIG. 9 also shows the flow rate 244 of the VAD 14 during the measurement of the raw accelerations. To enhance legibility of FIG. 9, a constant acceleration offset has been combined with each of the acceleration components (i.e., 300 mg added to the X-axis mean normalized acceleration 246, 100 mg has been added to the Y-axis mean normalized acceleration 248, 100 mg has been subtracted from the Z-axis mean normalized acceleration 250, and 300 mg has been subtracted from the magnitude 252 of the total mean normalized acceleration) so as to separate the plotted components.

Figure 10:
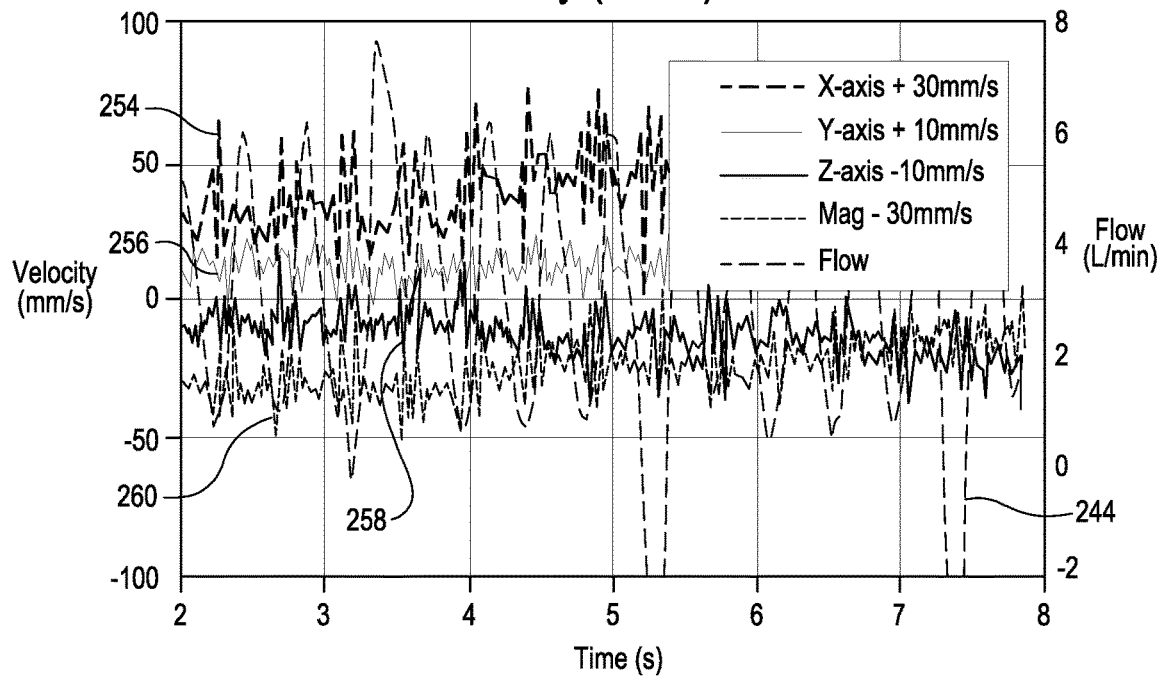
FIG. 10 is a plot of velocities of the VAD generated from the accelerations of FIG. 8.

FIG. 10 is a plot of velocities of the VAD 14 generated via integration of the mean normalized accelerations of FIG. 9. The output from at least three accelerometers (or one accelerometer and one gyroscope) can be integrated to determine the corresponding three-dimensional velocity. With fewer accelerometers, significant amounts of rotational motion may induce significant levels of error in the resulting three-dimensional velocity. While one accelerometer can provide reasonable estimates of the velocity if the rotational motions are insignificant, rotational motions of a VAD may be significant. For example, if the beating of the heart rocks the accelerometer back and forth in a motion that includes rotation, an error due to centripetal acceleration may accumulate. The error may be quite small for a time, but may grow in size over time. In many embodiments, acceleration due to gravity is filtered out prior to integrating the accelerations to determine the three-dimensional velocity. The velocities shown include X-axis velocity 254, Y-axis velocity 256, Z-axis velocity 258, and total velocity 260. FIG. 10 also shows the flow rate 244 of the VAD 14 during the measurement of the raw accelerations. To enhance legibility of FIG. 10, a constant velocity offset has been combined with each of the velocity components (i.e., 30 mm/sec added to the X-axis velocity 254, 10 mm/sec has been added to the Y-axis velocity 256, 10 mm/sec has been subtracted from the Z-axis velocity 258, and 30 mm/sec has been subtracted from the total velocity 260) so as to separate the plotted components.

Figure 11:
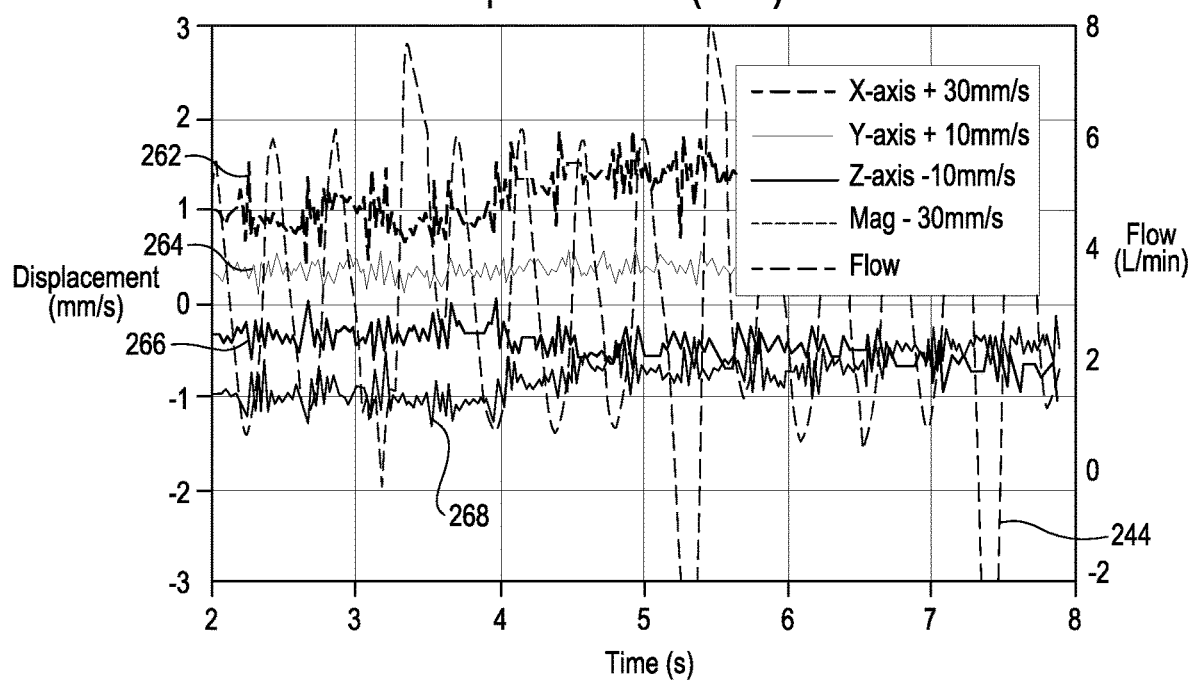
FIG. 11 is a plot of displacements of the VAD generated from the velocities of FIG. 10.

FIG. 11 is a plot of displacements of the VAD 14 generated via integration of the velocities of FIG. 10. The displacements shown include X-axis displacement 262, Y-axis displacement 264, Z-axis displacement 266, and total displacement 268. FIG. 11 also shows the flow rate 244 of the VAD 14 during the measurement of the raw accelerations. To enhance legibility of FIG. 11, a constant displacement offset has been combined with each of the displacement components (i.e., 1 mm added to the X-axis displacement 262, 0.3 mm has been added to the Y-axis displacement 264, 0.3 mm has been subtracted from the Z-axis displacement 266, and 30 mm/sec has been subtracted from the total displacement 268) so as to separate the plotted components.

Pump/Patient Orientation

In many embodiments, the output from the accelerometer 210 includes acceleration due to gravity and is therefore indicative of the orientation of the VAD 14, and therefore also the patient 12, relative to vertical. Any suitable approach can be used to process the output from the accelerometer 210 to determine the orientation of the patient 12 and/or the VAD 12 relative to vertical. For example, each of the X-axis acceleration 236, Y-axis acceleration 238, and Z-axis acceleration 240 can be processed to calculate a respective running average having a suitable time period (e.g., 10 to 15 seconds) corresponding to an X-axis gravity induced acceleration, a Y-axis gravity induced acceleration, and a Z-axis gravity induced acceleration, respectively. The X-axis gravity induced acceleration, Y-axis gravity induced acceleration, and the Z-axis gravity induced acceleration define a gravity vector that indicates the orientation of the accelerometer relative to vertical. Any suitable approach can be used to process the gravity vector to generate an indication of the orientation of the patient relative to a suitable reference axis or reference direction. For example, the gravity vector can be transformed from the accelerometer axis system to a patient reference axis system, for example, with a patient X-axis extending forward relative to the patient's thorax, a patient Y-axis extending to the left relative to the patient's thorax, and a patient Z-axis extending toward the top of the patient's thorax. As another example, reference gravity orientation vectors corresponding to known orientations of the patient 12 and/or the VAD 14 can be generated by placing the patient 12 and/or the VAD 14 in known orientations relative to vertical (e.g., standing upright, laying horizontal on the patient's left side, laying horizontal on the patient's right side, laying horizontal on the patient's back, and laying horizontal on the patient's stomach). The gravity vector can be compared to each of one or more of the reference gravity orientation vectors using a known approach to determine a relative angle between the gravity vector and the respective reference gravity orientation vector. The resulting relative angle(s) are indicative of the orientation of the patient 12 and/or the VAD 14 relative to the reference orientations of the patient 12 and/or the VAD 14.

Lung/Diaphragm Motion

The patient's respiration rate and the diaphragm contraction amplitude can be determined by processing the accelerometer output using a suitable band-pass filter (e.g., approximately 0.2 to 1.0 Hz (12 to 60 breaths per minute)) to isolate accelerations due to respiration. The resulting accelerations due to respiration can then be processed to determine corresponding respiration rate and diaphragm contraction amplitude. Frequency range and direction of movement can be used to isolate respiratory motion. In addition, accelerations due to respiration will typically have lower amplitudes (1 to 10 mg) and a regular pattern.

Heart Wall Motion

In some embodiments, the motion of the ventricular heart wall is monitored by processing the accelerometer output using a suitable band-pass filter (e.g., primary left ventrical wall motion range should be 0.5 to 3 Hz (30 to 180 BPM)) to isolate accelerations due to the ventricular heart wall motion. The heart wall motion can be processed to determine cardiac cycle timing, ventricle contractile strength, and ventricle contractile efficiency. Direction (z-axis, in line with the inflow cannula), frequency range, and timing regularity can be used to isolate LV wall motion. Transitions from periods of low accelerations to high accelerations (or changes in acceleration, jerk) can be used to indicate the start of a cardiac cycle (start of systole). Maximum acceleration can be used to estimate contractile strength. Contractile strength combined with min/mean/max flow through the pump can then be used to estimate contractile efficiency. The ventricle contractile strength and ventricle contractile efficiency can be monitored to monitor health of the patient's heart (e.g., detect signs of recovery or weakening). The heart wall motion can also be monitored to detect arrhythmia. Irregular cardiac cycle timing periods (start of systole) can be used to detect arrhythmia. In addition, heart rates above and below a normal range can be used to detect arrhythmia.

Heart Sounds

In some embodiments, the accelerometer output is processed to detect and/or measure heart sounds. The heart sounds that can be detected and/or measured include a first sound ($S_1$) generated by closing of the atrioventricular valves during ventricular contraction and a second sound ($S_2$) generated by closing of the semilunar valves during ventricular diastole. In some patients, the occurrence of aortic insufficiency (aka aortic regurgitation) generates a corresponding sound that can be detected via the accelerometer 210. In some embodiments, the accelerometer output is processed using a suitable band-pass filter (e.g., 50 to 500 Hz) to isolate accelerations due to the heart sounds. The accelerations due to the heart sounds can then be processed to detect/measure the heart sounds. The heart sounds can be used to monitor the cardiac cycle timing of the heart, as well as to monitor the patient for the occurrence of aortic insufficiency.

Pump Monitoring

In some embodiments, the accelerations measured by the accelerometer 210 include accelerations induced via operation of the VAD 14. The induced accelerations can include accelerations induced via vibrations of the rotor 140, speed of the rotor 140, change in speed of the rotor 140, and/or mass/balance of the rotor 140. Accelerations can also be induced as the result of ingestion of an object, by the VAD 14 such as a blood clot. Accelerations can also be induced by a suction event, which can occur when the VAD 14 over-extracts blood from the ventricle. In some embodiments, the accelerometer output is processed using a suitable band-pass filter (e.g., 0.5 to 3.0 Hz) to isolate accelerations induced via operation of the VAD 14. The accelerations induced via operation of the VAD 14 can be processed to monitor for excessive rotor vibration, ingestion of an object, and/or the occurrence of a suction event. For example, a suitable band-pass filter can be applied around the operating rotor speed (50-150 Hz) and potentially the subsequent harmonics. Changes in vibration amplitude (specifically increases) of the resulting filtered accelerations can be indicative of a rotor imbalance caused by either an ingested thrombus or thrombus forming on the rotor. Suction events can be detected via the combined occurrence of three events: (1) changes in LV wall motion (accelerometer), (2) low average flow through the pump (which can be detected via rotor drive current), and (3) low minimal flow fluctuations (which can be detected via the occurrence of small changes in drive current).

In some embodiments, the cardiac cycle timing of the patient is detected via monitoring of drive current supplied to the VAD 14, rotational speed of the rotor 140, flow rate of blood through the VAD 14, and/or pressure differential across the rotor 140. For example, during ventricular systole, variation in the ventricular pressure induces corresponding changes in the drive current supplied to the VAD 14 for a given rotational speed of the rotor 140. In some embodiments, the rotation speed of the rotor 140 is kept constant over one or more cardiac cycles to avoid inducing changes in the drive current due to changes in the rotational speed of the rotor 140. By monitoring the drive current supplied to the VAD 14, the cardiac cycle timing can be detected via detection of the time periods corresponding to ventricular systole. For example, in many embodiments the rotor drive current essentially follows a sinusoidal shape throughout the cardiac cycle. Peak flows (and drive current) occur at maximum left ventricle pressure, which is in the middle of systole. Minimum flows (min drive current) occur at the lowest left ventricle pressure, which is the start of diastole. In summary, the start of diastole can be detected by detecting the minimum drive current. Peak systole can be detected by detecting maximum drive current. Start of systole can be detected by detecting a sudden change in drive current slope (dI/dt) at the end of diastole.

Pump Control Based on Patient Activity Level

In some embodiments, the output of the accelerometer 210 is processed to measure an activity level of the patient 12, including deducing the patient's circadian rhythm. In some embodiments, the output of the VAD 14 is varied based on the measured activity level so as to provide increased support in response to an increase in the measured activity level and decreased support in response to a decrease in the activity level. In some embodiments, the average rotational speed of the rotor 140 is increased to increase the output of the VAD 14 and the average rotational speed is decreased to decrease the output of the VAD 14.

The output of the accelerometer 210 can be processed to measure a number of different patient physiological processes that are indicative of the activity level of the patient 12. For example, the accelerometer output can be processed using suitable approaches, such as those described herein, to measure respiration rate, diaphragm contraction amplitude, ventricle contraction amplitude, heart rate, vibration from walking/running, and/or orientation of the patient 12. The activity level of the patient 12 can be defined to be a suitable function of one or more of the respiration rate, the diaphragm contraction amplitude, the ventricle contraction amplitude, the heart rate, and/or the orientation of the patient 12.

Pump Synchronization with Patient Heart Cycle

In some embodiments, the output of the accelerometer 210 is processed to detect/measure the cardiac cycle timing for use in synchronization of operation of the VAD 14 with the cardiac cycle timing. The cardiac cycle timing can be determined based on any suitable indicator determined via processing of the accelerometer output, such as heart wall motion and heart sounds. Additionally, the cardiac cycle timing can be determined, as described herein, based on pump operating parameters, such as current, pump speed, and/or flow rate.

Figure 12:
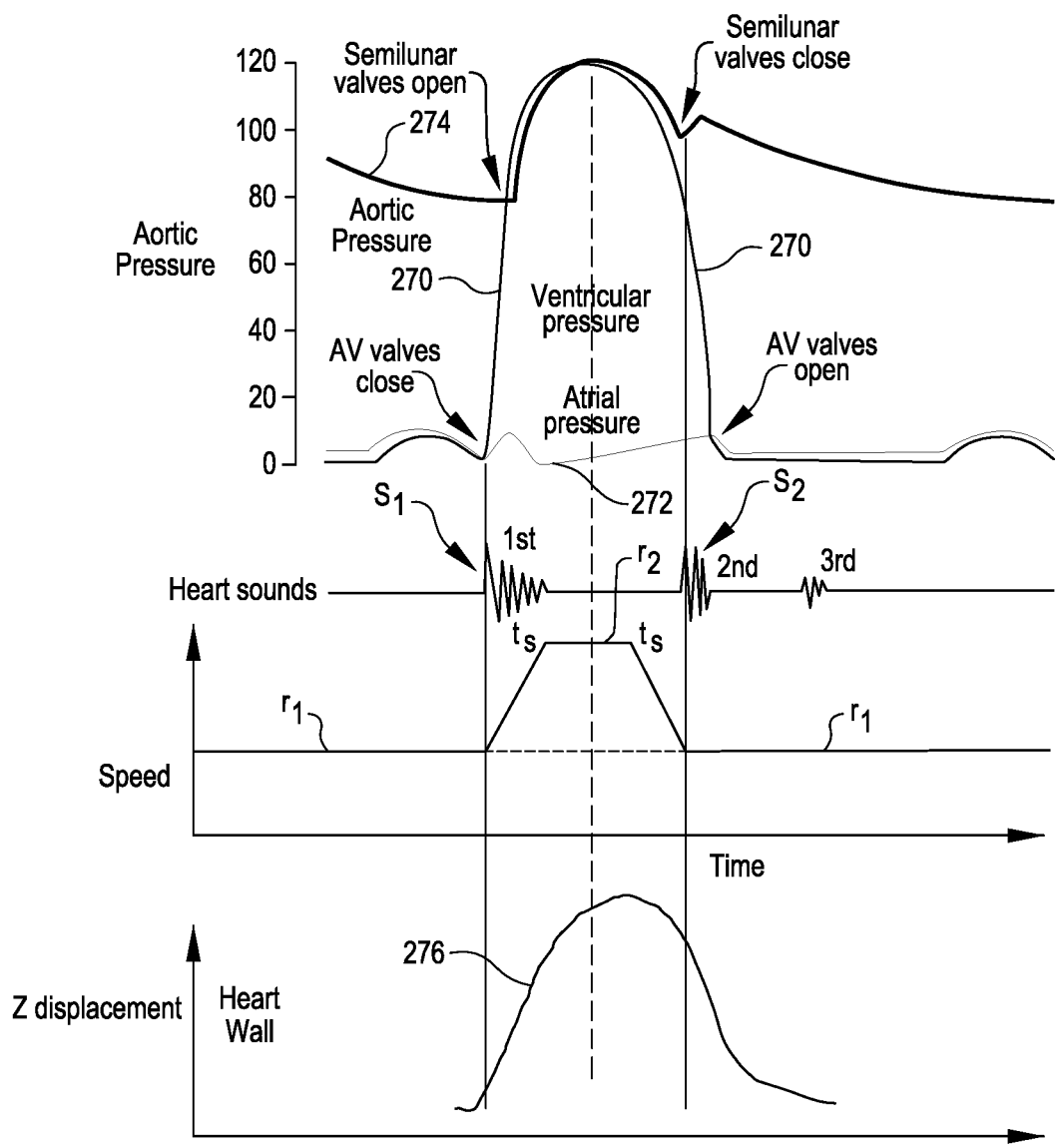
FIG. 12 illustrates synchronization of speed variation of the VAD of FIG. 3 with ventricular systole based on heart sounds, ventricular wall motion, and/or pump operating parameters, in accordance with many embodiments.

FIG. 12 illustrates synchronization of speed variation of the VAD 14 with ventricular systole based on heart sounds, ventricular wall motion, and/or pump operating parameters, in accordance with many embodiments. At the beginning of the cardiac cycle, both the atria and ventricles are relaxed (diastole). Blood flows into the atriums and into the ventricles from the atriums. Contraction of the atria (atrial systole) pumps additional blood from the atriums into the ventricles. Atrial systole ends prior to ventricular systole. During ventricular systole, each of the ventricular pressures 270 (only one shown for clarity) increases over the respective atrial pressure 272 (only one shown for clarity) thereby causing the respective atrial valve to close. The closing of the atrial valves generates the first heart sound ($S_1$). Further contraction of the respective ventricle increases the ventricular pressure 270 to above the respective output blood vessel pressure (e.g., aortic pressure 274), thereby causing the respective semilunar valve to open and blood to flow out of the ventricle. Ventricular relaxation (ventricular diastole) follows ventricular systole. As the ventricles relax, each of the ventricular pressures 270 drops below the respective output blood vessel pressure, thereby causing the respective semilunar valve to close. The closure of the semilunar valves generates the second heart sound ($S_2$). Further relaxation of the ventricles decreases each of the ventricular pressures below the respective atrial pressure (e.g., left atrial pressure 272), thereby causing the atrial valves to open.

Heart wall motion 276 during contraction of the ventricles during ventricular systole induces accelerations of the VAD 14 that are measured by the accelerometer 210. In the illustrated embodiment, the heart wall motion induced acceleration of the VAD 14 is primarily reflected in the Z-axis acceleration 240 measured by the accelerometer 210. Accordingly, the Z-axis displacement 266 can be processed to monitor the heart wall motion 276 to measure timing and strength of each ventricular systole, and thereby indicating cardiac cycle timing. Detection of the heart sounds ($S_1$ and $S_2$) can also be used to determine the cardiac cycle timing, either alone or in combination with the timing of ventricular systole determined via assessment of the heart wall motion 276.

In some embodiments, the VAD 14 is operated so as to vary output of the VAD 14 in synchronization with the cardiac cycle timing. For example, in some embodiments, the VAD 14 is operated to pump blood at a greater rate during ventricular systole than pumped by the VAD 14 during the rest of the cardiac cycle. In many embodiments, the rotation speed of the rotor 140 is varied to vary the rate that blood is pumped by the VAD 14. Any suitable variation of the output of the VAD 14 can be used. For example, as shown in FIG. 12, the rotational speed of the rotor 140 can be varied during ventricular systole so as to increase the output of the VAD 14 during ventricular systole. In the illustrated embodiment, the rotational speed of the rotor 140 varied during ventricular systole (i.e., increased from a first rotational speed (r1) to a second rotational speed (r2), maintained at the second rotational speed (r2) for a period of time, and then reduced back down to the first rotational speed (r1)).

Any suitable approach can be used to control timing of the variation in output of the VAD 14. For example, cardiac cycle timing observed during one or more previous cardiac cycles can be used to control timing of the variation in output of the VAD 14 during a current cardiac cycle. As another example, when sufficiently fast processing is utilized, cardiac cycle timing for a target cardiac cycle can be used to control timing of the variation in output of the VAD 14 during the target cardiac cycle.

Methods

FIG. 13 is a simplified schematic diagram of a method 300 in which accelerations of a VAD are measured and used to control operation of the VAD, monitor the patient in which the VAD is implanted, and/or monitor operation of the VAD. Any suitable circulation assist system that includes a VAD, such as the circulation assist systems described herein, can be used to practice the method 300. Any suitable combination of the below described acts of the method 300 can be employed in any suitable order. For example, any suitable set of the acts of the method 300 can be employed to control operation of the VAD based on patient activity level. Any suitable set of the acts of the method 300 can be employed to control operation of the VAD to vary output of the VAD in synch with a patient's cardiac cycle timing. Any suitable set of the acts of the method 300 can be employed to monitor the patient. And any suitable set of the acts of the method 300 can be employed to monitor operation of the VAD.

In act 302, accelerations of the VAD are measured. Any suitable approach can be used to measure the acceleration of the VAD. For example, in the VAD 14, the accelerations of the VAD 14 are measured via the accelerometer 210.

In act 304, the measured accelerations of the VAD are processed to monitor the orientation of the VAD and/or a patient in which the VAD is implanted. For example, the measured accelerations can be processed as described herein to monitor the orientation of the VAD and/or the patient.

In act 306, the measured accelerations of the VAD are processed to track the patient's cardiac cycle timing. For example, the measured accelerations can be processed as described herein to track the patient's cardiac cycle timing.

In act 308, operating parameters of the VAD are processed to track the patient's cardiac cycle timing. For example, operating parameters of the VAD (e.g., drive current) can be processed as described herein to track the patient's cardiac cycle timing.

In act 310, the measured accelerations are processed to monitor the patient's activity level. For example, the measured accelerations can be processed to monitor respiration rate, diaphragm contraction amplitude, heart rate, ventricle contraction amplitude, and/or the patient's orientation to monitor the patient's activity level as described herein.

In act 312, operation of the VAD is controlled in synch with the patient's cardiac cycle timing. For example, operation of the VAD 14 can be controlled to increase output of the VAD 14 during ventricular systole as described herein.

In act 314, operation of the VAD is controlled based on the patient's activity level. For example, the VAD 14 can be operated as described herein to increase output of the VAD 14 in response to an increase in patient activity level and to decrease output of the VAD 14 in response to a decrease in patient activity level.

In act 316, the measured accelerations are processed to generate VAD monitoring data. For example, the measured accelerations of the VAD 14 can be processed as described herein to generate VAD monitoring data indicative of mass/balance of the rotor 140, detect ingestion of an object (e.g., a blood clot) by the VAD 14, and/or detect a suction event.

In act 318, the measured accelerations are processed to generate patient monitoring data. For example, the measured accelerations of the VAD 14 can be processed as described herein to generate patient monitoring data indicative of patient orientation, heart rate, respiration rate, ventricular contraction strength and/or efficiency, presence of absence of arrhythmia, patient activity level, and/or presence or absence of aortic insufficiency.

In act 320, the patient monitoring data is output for subsequent processing and/or display. For example, the patient monitoring data can be stored in the VAD 14 and output to the system monitor 32 via the external system controller 20, or stored in the external system controller 20 and output directly to the system monitor 32.

In act 322, the VAD monitoring data is output for subsequent processing and/or display. For example, the VAD monitoring data can be stored in the VAD 14 and output to the system monitor 32 via the external system controller 20, or stored in the external system controller 20 and output directly to the system monitor 32.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method of controlling operation of a ventricular assist device (VAD) implanted within a patient having a heart, the method comprising:
   maintaining attachment of a housing of the VAD to a ventricular heart wall of the heart so that motion of the ventricular heart wall is transferred to the housing;
   processing, by a controller, output of an accelerometer supported by the housing to measure accelerations of the VAD, wherein the VAD comprises the accelerometer;
   processing, by the controller, the accelerations of the VAD to measure at least one of a respiratory activity of the patient or a cardiac cycle timing of the patient; and
   controlling, by the controller, operation of the VAD based on at least one of the respiratory activity or the cardiac cycle timing.

2. The method of claim 1, comprising:
processing the accelerations of the VAD to calculate a running average of the accelerations of the VAD based on a running average time period;
processing the running average of the VAD to determine an orientation of the patient; and
controlling the operation of the VAD based on the orientation of the patient.

3. The method of claim 2, wherein the orientation of the patient is measured relative to vertical.

4. The method of claim 3, comprising comparing the orientation of the patient to reference orientations of the patient to determine a respective relative angle between the orientation of the patient and each of one or more reference orientations of the patient.

5. The method of claim 4, wherein the one or more reference orientations of the patient comprise standing upright and laying horizontal.

6. The method of claim 4, wherein the one or more reference orientations of the patient comprise standing upright, laying horizontal on the patient's right side, laying horizontal on the patient's left side, laying horizontal on the patient's stomach, and laying horizontal on the patient's back.

7. The method of claim 1, comprising:
processing the accelerations of the VAD using a band-pass filter to isolate accelerations of the VAD due to respiration;
processing the accelerations of the VAD due to respiration to measure the respiratory activity; and
controlling the operation of the VAD based on the respiratory activity.

8. The method of claim 7, wherein:
the band-pass filter is configured to isolate accelerations of the VAD due to respiration in a range from 12 to 60 breaths per minute; and
the respiratory activity of the patient comprises a respiration rate of the patient.

9. The method of claim 8, wherein the respiratory activity of the patient comprises a diaphragm contraction amplitude of the patient.

10. The method of claim 1, comprising:
processing the accelerations of the VAD to determine the cardiac cycle timing; and
controlling the operation of the VAD based on the cardiac cycle timing.

11. The method of claim 10, comprising:
processing the accelerations of the VAD using a band-pass filter to isolate accelerations of the VAD due to the motion of the ventricular heart wall;
processing the accelerations of the VAD due to the motion of the ventricular hear wall to determine the cardiac cycle timing; and
processing the motion of the ventricular heart wall to determine the cardiac cycle timing.

12. The method of claim 10, comprising synchronizing a speed variation of the VAD with the cardiac cycle timing.

13. The method of claim 10, comprising synchronizing a variation of a flow rate of blood pumped by the VAD with the cardiac cycle timing.

14. The method of claim 1, comprising:
processing the accelerations of the VAD using a band-pass filter to isolate accelerations of the VAD due to the motion of the ventricular heart wall; and
processing the accelerations of the VAD due to the motion of the ventricular heart wall to determine ventricle contractile strength and/or ventricle contractile efficiency to monitor health of the patient's heart.

15. The method of claim 1, comprising:
processing the accelerations of the VAD using a band-pass filter to isolate accelerations of the VAD due to the motion of the ventricular heart wall; and
processing the accelerations of the VAD due to the motion of the ventricular heart wall to monitor for an occurrence of arrhythmia.

16. The method of claim 1, comprising monitoring the cardiac cycle timing for an occurrence of arrhythmia.

17. The method of claim 1, comprising:
processing the accelerations of the VAD using a band-pass filter to isolate accelerations of the VAD due to heart sounds of the patient; and
processing the accelerations of the VAD due to the heart sounds of the patient to determine the cardiac cycle timing.

18. The method of claim 1, comprising:
processing the accelerations of the VAD using a band-pass filter to isolate accelerations of the VAD due to heart sounds of the patient; and
processing the accelerations of the VAD due to the heart sounds of the patient to monitor for an occurrence of aortic insufficiency.

19. The method of claim 1, wherein the processing of the accelerations of the VAD comprises using a band-pass filter to isolate accelerations induced via operation of the VAD.

20. The method of claim 19, comprising processing the accelerations induced via operation of the VAD to monitor for one or more of excessive vibration of a rotor of the VAD, ingestion of an object by the VAD, and an occurrence of a suction event.

* * * * *